(12) United States Patent
Golyshina et al.

(10) Patent No.: US 8,003,357 B2
(45) Date of Patent: Aug. 23, 2011

(54) ACIDOPHILIC ENZYMES

(75) Inventors: Olga Golyshina, Wolfenbuettel (DE);
Peter Golyshin, Wolfenbuettel (DE);
Kenneth Timmis, Wolfenbuettel (DE);
Manuel Ferrer, Madrid (ES)

(73) Assignee: Helmholtz-Zentrum Fuer Infektionsforschung GmbH, Braunschweig (DE)

( * ) Notice: Subject to any disclaimer, the term of this patent is extended or adjusted under 35 U.S.C. 154(b) by 910 days.

(21) Appl. No.: 11/885,109

(22) PCT Filed: Mar. 3, 2006

(86) PCT No.: PCT/EP2006/060450
§ 371 (c)(1),
(2), (4) Date: Nov. 29, 2007

(87) PCT Pub. No.: WO2006/094943
PCT Pub. Date: Sep. 14, 2006

(65) Prior Publication Data
US 2010/0196965 A1 Aug. 5, 2010

(30) Foreign Application Priority Data
Mar. 3, 2005 (EP) .................................... 05101628

(51) Int. Cl.
*C12N 9/00* (2006.01)
*C12P 19/34* (2006.01)
*C12Q 1/68* (2006.01)
*C07H 21/04* (2006.01)

(52) U.S. Cl. ......... 435/183; 435/6; 435/91.52; 536/23.2

(58) Field of Classification Search .................. None
See application file for complete search history.

(56) References Cited

U.S. PATENT DOCUMENTS 5,506,137 A * 4/1996 Mathur et al. ............. 435/252.3

OTHER PUBLICATIONS

DNA ligase, UniProt Accession No. Q6L195, created Dec. 21, 2004.*
Database Geneseq, "Bacterial Polypeptide #10965" XP002416599, Database Accession No. ADS21932, Dec. 2, 2004.
Database UniProt, "Alpha Glucosidase (EC 3.2.1.20)", XP002416600, Database Accession No. Q5K3Q3, Feb. 15, 2005.
Database UniProt, "Carboxylesterase" XP002416601, Database Accession No. Q41TF6, Sep. 27, 2005.
Database UniProt, "Alpha-D-Glucoside Glucohydrolase 1 (EC 3.2.1.20)", XP002416602, Database Accession No. Q2PCE3, Feb. 7, 2006.
Database UniProt, "Alpha-D-Glucoside Glucohydrolase 2 (EC 3.2.1.20)", XP002416603, Database Accession No. Q2PCE2, Feb. 7, 2006.
Database UniProt, "Mandelate Racemase/Muconate Lactonizing Enzyme", XP002416604, Database Accession No. Q41V65, Sep. 27, 2005.
Database UniProt, "Acetyl Esterase", XP002416605, Database Accession No. Q6KZ86, Jul. 5, 2004.
Manuel Ferrer et al., "A Novel Alpha-Glucosidase from the Acidophilic Archaeon Ferroplasma Acidiphilum Strain Y with High Transglycosylation Activity and an Unusual Catalytic Nucleophile", *Biochemical Journal*, vol. 391, No. 2, Oct. 2005, pp. 269-276, XP002416589 ISSN: 0264-6021.
O.V. Golyshina et al., "Ferroplasma Acidiphilum Gen. Nov., Sp., Nov., An Acidophilic, Autotrophic, Ferrous-Iron-Oxidizing, Cell-Wall-Lacking, Mesophilic Member of the Ferroplasmaceae Fam. Nov., Comprising a Distinct Lineage of the Archaea", *International Journal of Systematic and Evolutionary Microbiology*, vol. 50, No. 3, 2000, pp. 997-1006. XP001117770 ISSN: 1466-5026.
O.V. Golyshina et al., "The 'pH Optimum Anomaly' of Intracellular Enzymes of Ferroplasma Acidiphilum", *Environmental Microbiology*, vol. 8, No. 3, Mar. 2006, pp. 416-425. XP002416590 ISSN: 1462-2912.
Bertus Van Den Burg, "Extremophiles as a Source for Novel Enzymes", *Current Opinion in Microbiology*, vol. 6, No. 3, Jun. 2003, pp. 213-218. XP002416591 ISSN: 1369-5274.
Manuel Ferrer et al., "A Purple Acidophilic Di-Ferric DNA Ligase from Ferroplasma", *PNAS*, Jul. 1, 2008, vol. 105, No. 26, pp. 8878-8883.

* cited by examiner

*Primary Examiner* — Anand Desai
*Assistant Examiner* — Iqbal H Chowdhury
(74) *Attorney, Agent, or Firm* — Greer, Burns & Crain Ltd.

(57) ABSTRACT

The present invention relates to enzymes having catalytic activity at a pH below 5.0. The present invention provides hydrolyzing enzymes obtainable from archaeobacteria, in detail to hydrolytic enzymes obtainable from the archaeobacterium *Ferroplasma acidiphilum*. In general, the present invention provides enzymes which are active and stable at acidic pH values, especially at pH values from 1 to 4, especially in the range of pH 2 to 3, obtainable from *Ferroplasma acidiphilum*, especially to an esterase, glycosidases and a DNA ligase. In addition to stability and activity at low pH values, the enzymes according to the present invention are all dependent on $Fe^{2+}$ for their catalytic activity.

4 Claims, 12 Drawing Sheets

Figure 1:
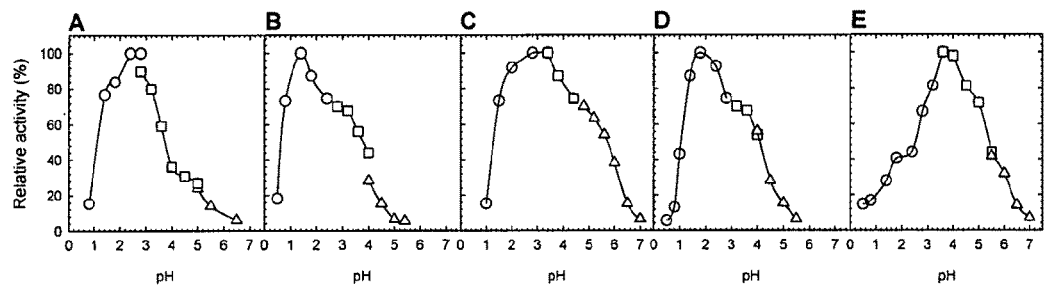

Figure 11: Sequence data obtained from *Ferroplasma acidiphilum*:

Seq. ID No 1: ligFA

CDS
ATGACAAAATCTTATAATATACTATATGATTATTATTTAATGTTATTTTCAGAAGC
CAGCAAAAAATTCATGGAGATGGAATCGACAACGAAGAGGCTTGAACTCACATC
AATACTGGGTTCATTGCTTGAAAATGCAGGGGATGACCTGAAGGAACTGGTATAT
TTAATACAGGGCAAGCTGGCACCGGATTATGAGGGTATAGAATTTGGAGTTTCGG
GGAAGCTTATAGTGAAATCCCTTGCAGCCATATCCGGAATGGATGAGGAAGAAG
TCAACAAATTGTTTTACAAGAATGGCGACCTTGGTATAACTGCCTCTGAAATCAG
GGAAAAAATGGAACAGAAGCCACTTTTCAGGGAAGACCTTACCGTACACTATGT
GTATACAAGGCTTATGGAACTTGCAAATCAGCAGGGCATGGAAGTGTAAAGGG
GAAAACAGATATTTATGCGGACCTCATGGTAAATTCATATCCTGAAGATATAAAG
TATATTACGAGGATAATCATGGGGAAACTCAGGTTAGGCGTTGCAGATTCCACAA
TACTTGATTCCCTGGTGCATGCATTTTTCTCTAAAGATAATGCGGATATGGTAGAA
ACAGCTTACAATTTTCATCCAGACATAGGGCTTATAGCAACGCTCCTGCAGAAAG
GCGATATAAAGGCCATAAGCAACATAGGCCCTGAGCCATTGATTCCATTCAAGGT
AATGCTTGCAGAAAGGCTGAGGTCCATCGATGATATAAGGGAAAAAATGAACCA
CCACGTATCATTTGAGTATAAATATGATGGGCTCAGGACAGAGTTGCACAAAAAA
GGGGATAAAATTAAGATTTTTTCAAGAGGGCTTGAGGAAACAACTGAAAATTTCC
CGGATATTATAGAAAATTTCAAAAAGAGCTATTCATTTGAATCCATAATAATTGA
TGGAGAATCGGTTCCGTTTAATCCCGATACAGGGGAATTGTTCCCATTCCAGATG
GTTTCCAAAAGGAGGGGAAGAAAATATCAGATTACAGAAAAATCCACTGAAATA
CCCCTTGTTATGTTTATTTTTGATATACTTGAGCTCAATGGAAGGATACTTGTTAA
CCTCCCATACGAAGAAAGGCGTAAAATTCTTGAAGAAAATTTTGTAGATAATGAG
CACTTTAGGCTGGCAACAAGATTGTCCTCGGATGATTCTGAAGAGATTAACAAAT
TCTTTGAACAGAGCATAGAGGATGGGTGTGAAGGCATTGTTGCGAAGGATACATC
TGATGAATCTGTTTACCGTGCAGGGGCTCGTGGGTGGCTTTGGATAAAATTTAAA
AGGGATTATCAGAAAGAACTTGCGGATTCCATGGACCTGGTAATTATCGGTGCAT
TTAATGGCCGTGGAAGGAGGGCAGGGGCATACGGTGCACTCCTCATGGCATCAT
ATAACGAAGAAACACATGCATTCGAGTCAGTCACAAAACTGGGAACAGGATTCA
GTGATGAGGTATTATTTTCATTGCCAAAAATGCTCTCTGATCTTGTAAGAGACCAC
AAACCTGCTATGGTTGAATCAAAAATGGTTCCTGACATCTGGATATATCCACAGA
TAGTTATGGAAATCCAGGGAGCAGAAATTACTGTAAGCCCTATACATACATGTGC
TTTTGGAAAAATAGAGAAAGATTCCGGCCCTGCGTTAAGATTTCCCAGATTAATT
AAAATACGTGACGATAAAAACGCTGAAGACGCTACAACTACCAATGAAATTATA
GAACTTTATAAAATGCAGAAAAAAACAAAATAA

Seq. ID No 3: LigFA

MTKSYNILYDYYLMLFSEASKKFMEMESTTKRLELTSILGSLLENAGDDLKELVYLIQ
GKLAPDYEGIEFGVSGKLIVKSLAAISGMDEEEVNKLFYKNGDLGITASEIREKMEQK
PLFREDLTVHYVYTRLMELAKSAGHGSVKGKTDIYADLMVNSYPEDIKYITRIIMGK
LRLGVADSTILDSLVHAFFSKDNADMVETAYNFHPDIGLIATLLQKGDIKAISNIGPEP
LIPFKVMLAERLRSIDDIREKMNHHVSFEYKYDGLRTELHKKGDKIKIFSRGLEETTEN
FPDIIENFKKSYSFESIIIDGESVPFNPDTGELPFQMVSKRRGRKYQITEKSTEIPLVMFI
FDILELNGRILVNLPYEERRKILEENFVDNEHFRLATRLSSDDSEEINKFFEQSIEDGCE
GIVAKDTSDESVYRAGARGWLWIKFKRDYQKELADSMDLVIIGAFNGRGRRAGAYG
ALLMASYNEETHAFESVTKLGTGFSDEVLFSLPKMLSDLVRDHKPAMVESKMVPDI

WIYPQIVMEIQGAEITVSPIHTCAFGKIEKDSGPALRFPRLIKIRDDKNAEDATTTNEIIE
LYKMQKKTK

Seq ID No. 4: estFA

CDS
ATGCATTTAATGAATATGGTAGATCCGGATTTTAATTCGCTTATAGAATTGTCAAA
AAGTGCGGGAGATATGACGAAAATAGAGCCTGCTATGCTTAGAAATTTCCTTGAC
GAATCCTCACTGAGCTCCAGGGGGGCGCCAGTGGAGATAAAAGAGATCAAAGAT
TATAAAATAAAACTGGATGGGCGCACACTGAATGCCAGAATGTATGATGATAAT
AATGCAAAATCAGCTATTTTATATTACCATGGTGGAGGCTTTCTTTTCGGCAATAT
TGAAACATATGATAATTATTGCCGCTTCCTTGCTAAGGAGTCAGGGGTTAAGATT
ATATCTATTGAATACCGACTGGCACCGGAACATAAATTTCCAGATGCTTTCAATG
ATGCTTATGATTCGTTCCATTATATAGCTAAAAAGAAGAAAGATTTTGGAATAGA
AGGCAGAATAGGCGTAGCCGGTGATAGTGCCGGTGCAAATCTTGCAGCTGCATTA
TGCCTGAAATGCCGTGATGGGAAAACTGAAATGCCTGCTGTACAGGTATTGTTCT
ATCCAAGCCTTGCACCGGATAATTTCTCCAGATCTTTTATTGAGTATTCCGATAAC
TATGTCTTAACGGGAAAGATGATAAGATATTTCGGAAATATGTATTCAAAAAATA
TGCAGGATCTGATAAATCCATATTTCTCGCCCCTTGTTGCCGATGATTTTTCAAAT
CTTCCACCAGCCATAATGGTAACTAATGAATACGACCCTTTGAGAGACCCTGAAG
AAACATATGTTAAAAAACTCAGGGAAGCGGGAGTCAGGGCAGTTGGAATAAGGG
GGATAGGAATGATTCATGGCTCGGCCACTGACTTTGAGGTTTCTGATGGTGCCAG
AAACATTGTAAAAATGGTTGCCAGGATTATTCCTGACTATTTATAG

Seq ID No. 6: EstFA

MHLMNMVDPDFNSLIELSKSAGDMTKIEPAMLRNFLDESSLSSRGAPVEIKEIKDYKI
KLDGRTLNARMYDDNNAKSAILYYHGGGFLFGNIETYDNYCRFLAKESGVKIISIEYR
LAPEHKFPDAFNDAYDSFHYIAKKKKDFGIEGRIGVAGDSAGANLAAALCLKCRDGK
TEMPAVQVLFYPSLAPDNFSRSFIEYSDNYVLTGKMIRYFGNMYSKNMQDLINPYFSP
LVADDFSNLPPAIMVTNEYDPLRDPEETYVKKLREAGVRAVGIRGIGMIHGSATDFEV
SDGARNIVKMVARIIPDYL

Seq. ID No 7: αgluFA

Coding sequence of DNA fragment contained in bases 339-1934 (bold type)

TCCCAGTGCATTTGCAACGTATGCAAAATTCCCTGCAGTACCTGCAAATTTCTCTC
TAAGGGCCTTTACACCGGTAGCCTGGCCTGGAGACGGTAGAGATGGCACAGATA
GGGTTACATCTATATTTAAGTGGCCAAAGAAAGCCAAAAACTTCATAGCTAGCGA
TTGTAATTAAATATTTAACAAATTTGACCGGGAAAAGGAATATTTCCTATCAACT
GGAGCCGGCATCTATATTTCCCACAGCAATTTATTTTATATTGCTTAATTATTATC
ACATAGAAATAATATATAATACATTACATACTTTCACTATTTCAAAACATTTATAT
TGGTAAATTAACTCATTATATATATTGAATCATAAAGTTATAATTGCCGTTGC
**AGTTAGTGCAATTCTTATTGCAATGGTCTTTGCAGGTGCAAATATTCCCTATC
CGGGTTACAATCCAACCGATCATCTCATATCTGGAAAACACCCTATTTCCAA
TGTATCAGAGGTACCCAAGAATTTTACTTTATCTGGAAACGTATCTAATTCTA
ATAATAATTTGCCACTTTCCGGAACTATAACAGTAAGCAATTCCACAATGTCC**

AGAACATTTAATACCAGCAGCAATGGAAGCTATAATATCACTCTCCCGCAAG
GGAATTATAGTATATCGTCTTCAATACCTGGATTTCAAAATTATTCATCCACA
ATCAATCTGGATAGCAATAAAACGCAGAATATATCAACGCCTCCTGCTACTA
CCATAGGAAATGGAATTAATCAGGTTCCAGGTTCTACCAATGTGTCAACACT
GGTTCCATATCTCAATAATAGTATTATGTCTGGAGGGCTTAATACTGACAAT
ATAACCGGAACATTTGATAAAAATATCACAATAGATCTGGGCAAGAAATTAA
ACAATACACAATTTGTTGTATTGATGAAGTTAGACGGTGCAGTATATAGCTA
TAATTGGGTGACAAACGGAAGCGGGATGGCGAAATTATTCCTTAAATATTCC
GGAAATTATACAATGTCCGCATATACACTGTATTATAATTCTAGTGTAATTCA
TTACAATACTGCAAATAATGATACTGCCAGATTCAATATGACAGAGCGTATA
ACATTCATTTCCTCTGTTATTCTTCAAAGTGCAGTCCCATTACATGATAATTC
ATCAGTTGCAAACTCAACACTCACAGTCAAAGGGGAGTTTTCTCTGTACCT
TCCTTATCCGTTAACAGTAATTTAACAGGGACTTACTATAAATATGAGGTACC
CGTTGGTTTCTATAATTTTGCTTACAGTAATGCCCATTACGTTTCAAAAAATT
TTGGCGTTGATGTAACAGGAAACAGTACAGTAAATAAAACAATTGACCCTTA
TTTAATATCCATAAATATAAGGAATAATACCGGGAATACATTTAATTATACAC
TTGGTAGCACATTTTATAGTGGTAATGGCATACACATGGCTACTTCAGGCAT
AACCACCCTATTAGTGTTCCATGACGGTAAAATAGTATACGACAATACAATA
CTCCTAACCAGTGCAAATCCATACTACCAGCTTAACCTTACTATTAGCAACAA
AAATCTTACATTTAACGGCATTGAAACGGATTCGACAAATCTTTCCATTGTAT
ATTCAGGCAATGTAACTTCTAACTTTTATATTGCATCCCTCGAATTTGAAAAC
TTTAGCACATCTGCCACTAACGGAATGATAATTATTTCCGGTGCTGCGAGTG
GAAGCTACCCCCTAGACAGTGGATTATATACATACAATATGTCACAATCCCT
TCCAACATCAGCGGGCAACCTCACAATAAAACTCGTTTATGATAATGATTCT
AAGGTAAGCACAGATGGGCGTATGACTGTAGAGGTATATGGTTATAATATAT
CCACACTAGGAAATTATATTACGGAGTGATTTTTATTGCTATTCAAAAGAATG
TACAGAAAACAGAGAAAATTGAAGAGAAGACTAAAACTGTGTTGAAAATAAAAA
CAGTTGACGATATACCTGTAATAAAGGAAATGAGGAAGAAGATAGGGAATGGGG
AACGAAAGGAAGCAATAATATACGGGTACACAA

Seq. ID No. 9: αgluFA, coding sequence for αGluFA from Seq. ID No. 5

CDS
ATTAACTCATTATATATATTGAATCATAAAGTTATAATTGCCGTTGCAGTTAGTGC
AATTCTTATTGCAATGGTCTTTGCAGGTGCAAATATTCCCTATCCGGGTTACAATC
CAACCGATCATCTCATATCTGGAAAACACCCTATTTCCAATGTATCAGAGGTACC
CAAGAATTTTACTTTATCTGGAAACGTATCTAATTCTAATAATAATTTGCCACTTT
CCGGAACTATAACAGTAAGCAATTCCACAATGTCCAGAACATTTAATACCAGCAG
CAATGGAAGCTATAATATCACTCTCCCGCAAGGGAATTATAGTATATCGTCTTCA
ATACCTGGATTTCAAAATTATTCATCCACAATCAATCTGGATAGCAATAAAACGC
AGAATATATCAACGCCTCCTGCTACTACCATAGGAAATGGAATTAATCAGGTTCC
AGGTTCTACCAATGTGTCAACACTGGTTCCATATCTCAATAATAGTATTATGTCTG
GAGGGCTTAATACTGACAATATAACCGGAACATTTGATAAAAATATCACAATAG
ATCTGGGCAAGAAATTAAACAATACACAATTTGTTGTATTGATGAAGTTAGACGG
TGCAGTATATAGCTATAATTGGGTGACAAACGGAAGCGGGATGGCGAAATTATTC
CTTAAATATTCCGGAAATTATACAATGTCCGCATATACACTGTATTATAATTCTAG
TGTAATTCATTACAATACTGCAAATAATGATACTGCCAGATTCAATATGACAGAG
CGTATAACATTCATTTCCTCTGTTATTCTTCAAAGTGCAGTCCCATTACATGATAA
TTCATCAGTTGCAAACTCAACACTCACAGTCAAAGGGGAGTTTTCTCTGTACCTT
CCTTATCCGTTAACAGTAATTTAACAGGGACTTACTATAAATATGAGGTACCCGT

TGGTTTCTATAATTTTGCTTACAGTAATGCCCATTACGTTTCAAAAAATTTTGGCG
TTGATGTAACAGGAAACAGTACAGTAAATAAAACAATTGACCCTTATTTAATATC
CATAAATATAAGGAATAATACCGGGAATACATTTAATTATACACTTGGTAGCACA
TTTTATAGTGGTAATGGCATACACATGGCTACTTCAGGCATAACCACCCTATTAGT
GTTCCATGACGGTAAAATAGTATACGACAATACAATACTCCTAACCAGTGCAAAT
CCATACTACCAGCTTAACCTTACTATTAGCAACAAAAATCTTACATTTAACGGCA
TTGAAACGGATTCGACAAATCTTTCCATTGTATATTCAGGCAATGTAACTTCTAAC
TTTTATATTGCATCCCTCGAATTTGAAAACTTTAGCACATCTGCCACTAACGGAAT
GATAATTATTTCCGGTGCTGCGAGTGGAAGCTACCCCTAGACAGTGGATTATAT
ACATACAATATGTCACAATCCCTTCCAACATCAGCGGGCAACCTCACAATAAAAC
TCGTTTATGATAATGATTCTAAGGTAAGCACAGATGGGCGTATGACTGTAGAGGT
ATATGGTTATAATATATCCACACTAGGAAATTATATTACGGAGTGA

Seq. ID No 11: αGluFA

INSLYILNHKVIIAVAVSAILIAMVFAGANIPYPGYNPTDHLISGKHPISNVSEVPKNFT
LSGNVSNSNNNLPLSGTITVSNSTMSRTFNTSSNGSYNITLPQGNYSISSSIPGFQNYSS
TINLDSNKTQNISTPPATTIGNGINQVPGSTNVSTLVPYLNNSIMSGGLNTDNITGTFDK
NITIDLGKKLNNTQFVVLMKLDGAVYSYNWVTNGSGMAKLFLKYSGNYTMSAYTL
YYNSSVIHYNTANNDTARFNMTERITFISSVILQSAVPLHDNSSVANSTLTVKGGVFS
VPSLSVNSNLTGTYYKYEVPVGFYNFAYSNAHYVSKNFGVDVTGNSTVNKTIDPYLI
SINIRNNTGNTFNYTLGSTFYSGNGIHMATSGITTLLVFHDGKIVYDNTILLTSANPYY
QLNLTISNKNLTFNGIETDSTNLSIVYSGNVTSNFYIASLEFENFSTSATNGMIIISGAAS
GSYPLDSGLYTYNMSQSLPTSAGNLTIKLVYDNDSKVSTDGRMTVEVYGYNISTLGN
YITE

Seq. ID No 12: gluFA1

Coding sequence of DNA fragment contained in bases 621-1361 (bold type)

ACCCCACTCCTTTCACTTAATATCTTGGTATAGTTTTTTGAAAATATAGCATTATA
CATGTAATCAAAATCAATTAAAATATCAAGCTTTTCTTTGGAATAAGCATCAATA
ATTTCATCATAATTGTATCTATTACCATTCACTTCATGAAAATACTTTGTAATTTTA
ATCCCTTGATTCTCCAATTCATGAGCCTTTCGAATCAAAACTTCTTTTTTTGATTTA
TTATATATCTCGGGACTAGGCAAGTATACAATATTAAAATAATTATTTAATATTTT
TATAATATTTATTGTATGAGTTTGTGCCCCTCCGTAACTTGAAAAAATGTCAGGAC
CGGTTACACCAATATTCACGATACTTGTATCAATTTCGTATTAATAATATTTCTCA
AAATAATGTTTGAGATGATGTTTATAATCTAGACAATTTAAATGAACAGTAATTC
AAAAATTTATTTGATAATCAAGAAAATAATAACGGTATAAAATACTTTTATCTGA
GATTGCTAGAATCCATAATATAACACCATAATCAAATTATACAGATTAAGTCATT
CAGGTAATGGAAAACTATGTTTTACTGAGAAGCTTTATATTATAATATTATATGCT
ATTAAAATGGAAATTCAGGATATCGATTTAACTATTGTTTTAGCAACTCTTAA
CGAAATAGATAATCTTCCACGGCTCTGTTCTGATATCGATTCAATATTAAAAA
ATACGAAAATAAAGTATCAGTTATTATTTGTCGATGATAACAGTAGCGATGG
AACCAGAGAGTTTATTATAGAGTATTGCAATAAAAATAAATTATCAAAATATA
TTTTTAATGAATACAAGAAATCAACCCTTATAGCCAGATACCAGGGAATAAA
CAATGCAGATGGGAAATATATTATACTTATGGATTCAGATTTGCAACATCCC
CCAAAATATCTCTTAAATATATATAACAGTTTATTGAAACATAATGATATCGT
AATTGCCAGCAGATACGTTAAAGGTGGCAGTACCGGAAATCGCAAACCTATA
CGTGGCATTATATCACGTGGGGCATCTTTGATGGCACAACTACTATTGAAAA

GCAGCAGGCAGATAAAGGACCCCATATCGTGTTATATTGGCTTTAGAAAAGG
GCTGAAATTGGATATAGACGAAGGCTGGAGAGGCTATGAGATAGGTATTTTC
TTAAGGGCTAGCAATAATAATGTTAAGGTAAAGGAAATACCTTATCGATTTG
CGGAAAGGGAAAATGGAAAATCAAAAGTAACGTCCAGTGTAAAATTTTTAAG
AGTTTATATAATAGAATTATTATTGGCAAAAAGAGTTGAGATAAGAAATTATA
AACCAATTTTGTGATGTATATAATATAAAGTTAAATTGTAGTAATGGCATTGTAT
TCATTTGAGATTATTGTTTGTTCTTATTGAACCTTAATATAAATAAAAAGAACGAT
ATAGCAATGGCTATCCCTATTATTTTAAAGTATATTAAATCTATACTGATTAATCT
ATAATAATATAATGTAAATAGCTGAGTAGAACACAA

Seq. ID No. 14: gluFA, coding sequence for GluFA1 from Seq. ID No. 7

CDS
ATGGAAATTCAGGATATCGATTTAACTATTGTTTTAGCAACTCTTAACGAAATAG
ATAATCTTCCACGGCTCTGTTCTGATATCGATTCAATATTAAAAAATACGAAAAT
AAAGTATCAGTTATTATTTGTCGATGATAACAGTAGCGATGGAACCAGAGAGTTT
ATTATAGAGTATTGCAATAAAAATAAATTATCAAAATATATTTTTAATGAATACA
AGAAATCAACCCTTATAGCCAGATACCAGGGAATAAACAATGCAGATGGGAAAT
ATATTATACTTATGGATTCAGATTTGCAACATCCCCCAAAATATCTCTTAAATATA
TATAACAGTTTATTGAAACATAATGATATCGTAATTGCCAGCAGATACGTTAAAG
GTGGCAGTACCGGAAATCGCAAACCTATACGTGGCATTATATCACGTGGGGCATC
TTTGATGGCACAACTACTATTGAAAAGCAGCAGGCAGATAAAGGACCCCATATC
GTGTTATATTGGCTTTAGAAAAGGGCTGAAATTGGATATAGACGAAGGCTGGAG
AGGCTATGAGATAGGTATTTTCTTAAGGGCTAGCAATAATAATGTTAAGGTAAAG
GAAATACCTTATCGATTTGCGGAAAGGGAAAATGGAAAATCAAAAGTAACGTCC
AGTGTAAAATTTTTAAGAGTTTATATAATAGAATTATTATTGGCAAAAAGAGTTG
AGATAAGAAATTATAAACCAATTTTGTGA

Seq. ID No 16: GluFA1

MEIQDIDLTIVLATLNEIDNLPRLCSDIDSILKNTKIKYQLLFVDDNSSDGTREFIIEYCN
KNKLSKYIFNEYKKSTLIARYQGINNADGKYIILMDSDLQHPPKYLLNIYNSLLKHNDI
VIASRYVKGGSTGNRKPIRGIISRGASLMAQLLLKSSRQIKDPISCYIGFRKGLKLDIDE
GWRGYEIGIFLRASNNNVKVKEIPYRFAERENGKSKVTSSVKFLRVYIIELLLAKRVEI
RNYKPIL

Seq. ID No 17: gluFA2

Coding sequence of DNA fragment contained in bases 840-1985 (bold type)

GATCGTATTACATGATCGTAATATAATCCACTATAGTTTATTTTTCCTGCCCATGC
ACTCCAGTAATTTCTTGTTTCTTCCAGCCGTGTATATGATTCATATTGCCTTACATT
GCCAATTTGCCTTACTCCGCTTAATACAACAATCCATTCATGTGAACCTTTTTCCA
CTTTTATCCTGCTGTATACATTTCCATTTCCCTTTTTCAATTTAAGATTTGTGGAAA
TTCCAAGTGTGTCATCTGTACATGAGAAATATAACCATTTCTATCCCTGGTTATG
TTTGTTTTCCCTGAGCCAAAGTTAAAATGCGATTTTATATCTATTGATACTTCAAC
ATCAGAATATGGGGCCTCAATTAGCCGGTGTATCTCCGGAAACGTTATTGTGCTA
TATGATGATGTTGGAAGAAAATCTGTGAGCCTTAAAATTACCTGATTGTTATTTAC

```
AAACTCTGTTATAAGTATATTGGTTGATTCTTCGTAATACTGGTTGACATTGCTTT
CCATTACAGGGCTGGTCTTGAAATAACCACCATTTCTGGCATCAAGAATAGAATC
AAAGACAGGATTTGAATTAAAGTTGGGCAAACATGCCCAGTCAATAGTTCCATCT
ATACCAACAAGTGCTGCAGTGCGGTTATTTGCAATAAAACCGTGATTTGCAATCT
TTAAATAATCAGATCTGTATGCATCATGCAGATCGTAAAGCCCTCTGTATGTACC
CATGGTAAAATTGATAATAATAATATATAAAGAGTTTATCAGAAGCCAGAAATA
ATGCTAAATGGTAAAACTGGAAAATAGGAATAGATTTATAACCAGACGTATTATA
TTTTTATGAAAATAACTTACCACAAGCTAAAAATGCCACTGATAAGCCCATTC
ACAACCAGCTTCGGAACAGATGTAAACAAGGATGTTTATGTTTTCAAGCTTG
AACATAATGGAATAACTGCTTATTCTGAAAGTGTTACCGACGAAAATCCTTTT
TATGGCTCAGAAGATAATTATACAGTATTCCATATTGTAAAACAGTATCTTGC
ACCAGTAGTAAAAGGCCTTCCAGAGCCGGATGAATTCAATGAACAGGTAAAA
TTTATAAAAGGCAATAATATGGCAAAGCTTCCATGGAAATGCTTCTCTATG
ATTATTATGCAAAAGCAAATAAAAAATCCCTGGTAGATTACATAGGGCACAG
CAGGGGATATGCAAACGTTGGAATATCACTTGGAATGGATGATATAAACGTT
ACATTAAAGAAGATACAGGAAGCCCTTGACCGTGGATATAAAAGAATTAAAG
TCAAAATAATGAAGGGAAAGGAAATAGGTATACTAAGTGCTGTAAGGGACAA
TTTTCCGGATATAGTTTTAAGTGCAGACGCCAACAGCGATTATACCGAGAAG
GATTTTGATTTGATTAAAAAAATAGACAGATACAATCTTGTATATCTGGAGCA
GCCCCTGTACCATGATGATATAATATACCATTCAAGGCTTGCAAAGGGATTA
TCCACGCCATTATGCCTGGATGAATCTATTACTTCACCGGAGAAGGCACAGA
AAGCATTTGAAATGGGTGCGTGTAAGGTTATAAACATAAAAGAGGGAAGGCT
AGGCGGAATCGGAAATTCCTTAAAAGTTATGGGAATAGTGAAGGAATTCAAG
GGCCATGTATGGATTGGAGGAATGTTAGAAACTGGAATCGGAAGGTCCTTTA
ATGTTTCCATGGCATCTCTTTCTGATATTAATTATCCTGGAGACACATCGCCC
AATGACAAATACTTTAAAAATGACATAGTTAAGAATCCATTCACAATGGAAA
ATGGCACAATTAAGCCTAATAAGGGTACAGGCATCGGTGTTGAAATCAGTGA
AGAGTATCTAAAAAAATATACCGTTGAAGAGGGGATAATAGCATGAATAATG
TATTCCAGTATTTCAAAAGCCAGCAGGATTCAATGCTATCAGATTTAAAATCATT
AGTAGAGATGGAAA
```

Seq. ID No. 20: gluFA2, coding sequence for GluFA1 from Seq. ID No. 9

CDS
```
ATGAAAATAACTTACCACAAGCTAAAAATGCCACTGATAAGCCCATTCACAACCA
GCTTCGGAACAGATGTAAACAAGGATGTTTATGTTTTCAAGCTTGAACATAATGG
AATAACTGCTTATTCTGAAAGTGTTACCGACGAAAATCCTTTTTATGGCTCAGAA
GATAATTATACAGTATTCCATATTGTAAAACAGTATCTTGCACCAGTAGTAAAAG
GCCTTCCAGAGCCGGATGAATTCAATGAACAGGTAAAATTTATAAAAGGCAATA
ATATGGCAAAGCTTCCATGGAAATGCTTCTCTATGATTATTATGCAAAAGCAAA
TAAAAAATCCCTGGTAGATTACATAGGGCACAGCAGGGGATATGCAAACGTTGG
AATATCACTTGGAATGGATGATATAAACGTTACATTAAAGAAGATACAGGAAGC
CCTTGACCGTGGATATAAAAGAATTAAAGTCAAAATAATGAAGGGAAAGGAAAT
AGGTATACTAAGTGCTGTAAGGGACAATTTTCCGGATATAGTTTTAAGTGCAGAC
GCCAACAGCGATTATACCGAGAAGGATTTTGATTTGATTAAAAAAATAGACAGAT
ACAATCTTGTATATCTGGAGCAGCCCCTGTACCATGATGATATAATATACCATTC
AAGGCTTGCAAAGGGATTATCCACGCCATTATGCCTGGATGAATCTATTACTTCA
CCGGAGAAGGCACAGAAAGCATTTGAAATGGGTGCGTGTAAGGTTATAAACATA
AAAGAGGGAAGGCTAGGCGGAATCGGAAATTCCTTAAAAGTTATGGGAATAGTG
AAGGAATTCAAGGGCCATGTATGGATTGGAGGAATGTTAGAAACTGGAATCGGA
```

AGGTCCTTTAATGTTTCCATGGCATCTCTTTCTGATATTAATTATCCTGGAGACAC
ATCGCCCAATGACAAATACTTTAAAAATGACATAGTTAAGAATCCATTCACAATG
GAAAATGGCACAATTAAGCCTAATAAGGGTACAGGCATCGGTGTTGAAATCAGT
GAAGAGTATCTAAAAAAATATACCGTTGAAGAGGGGATAATAGCATGA

Seq. ID No 22: GluFA2

MKITYHKLKMPLISPFTTSFGTDVNKDVYVFKLEHNGITAYSESVTDENPFYGSEDNY
TVFHIVKQYLAPVVKGLPEPDEFNEQVKFIKGNNMAKASMEMLLYDYYAKANKKSL
VDYIGHSRGYANVGISLGMDDINVTLKKIQEALDRGYKRIKVKIMKGKEIGILSAVRD
NFPDIVLSADANSDYTEKDFDLIKKIDRYNLVYLEQPLYHDDIIYHSRLAKGLSTPLCL
DESITSPEKAQKAFEMGACKVINIKEGRLGGIGNSLKVMGIVKEFKGHVWIGGMLET
GIGRSFNVSMASLSDINYPGDTSPNDKYFKNDIVKNPFTMENGTIKPNKGTGIGVEISE
EYLKKYTVEEGIIA

SEQUENCE LISTING

<160> NUMBER OF SEQ ID NOS: 13

<210> SEQ ID NO 1
<211> LENGTH: 1788
<212> TYPE: DNA
<213> ORGANISM: Ferroplasma acidiphilum
<220> FEATURE:
<221> NAME/KEY: CDS
<222> LOCATION: (1)..(1788)
<223> OTHER INFORMATION: lig Fa

<400> SEQUENCE: 1

```
atg aca aaa tct tat aat ata cta tat gat tat tat tta atg tta ttt      48
Met Thr Lys Ser Tyr Asn Ile Leu Tyr Asp Tyr Tyr Leu Met Leu Phe
1               5                   10                  15 tca gaa gcc agc aaa aaa ttc atg gag atg gaa tcg aca acg aag agg      96
Ser Glu Ala Ser Lys Lys Phe Met Glu Met Glu Ser Thr Thr Lys Arg
                20                  25                  30 ctt gaa ctc aca tca ata ctg ggt tca ttg ctt gaa aat gca ggg gat     144
Leu Glu Leu Thr Ser Ile Leu Gly Ser Leu Leu Glu Asn Ala Gly Asp
            35                  40                  45 gac ctg aag gaa ctg gta tat tta ata cag ggc aag ctg gca ccg gat     192
Asp Leu Lys Glu Leu Val Tyr Leu Ile Gln Gly Lys Leu Ala Pro Asp
        50                  55                  60 tat gag ggt ata gaa ttt gga gtt tcg ggg aag ctt ata gtg aaa tcc     240
Tyr Glu Gly Ile Glu Phe Gly Val Ser Gly Lys Leu Ile Val Lys Ser
65                  70                  75                  80 ctt gca gcc ata tcc gga atg gat gag gaa gaa gtc aac aaa ttg ttt     288
Leu Ala Ala Ile Ser Gly Met Asp Glu Glu Glu Val Asn Lys Leu Phe
                85                  90                  95 tac aag aat ggc gac ctt ggt ata act gcc tct gaa atc agg gaa aaa     336
Tyr Lys Asn Gly Asp Leu Gly Ile Thr Ala Ser Glu Ile Arg Glu Lys
            100                 105                 110 atg gaa cag aag cca ctt ttc agg gaa gac ctt acc gta cac tat gtg     384
Met Glu Gln Lys Pro Leu Phe Arg Glu Asp Leu Thr Val His Tyr Val
        115                 120                 125 tat aca agg ctt atg gaa ctt gca aaa tca gca ggg cat gga agt gta     432
Tyr Thr Arg Leu Met Glu Leu Ala Lys Ser Ala Gly His Gly Ser Val
    130                 135                 140 aag ggg aaa aca gat att tat gcg gac ctc atg gta aat tca tat cct     480
Lys Gly Lys Thr Asp Ile Tyr Ala Asp Leu Met Val Asn Ser Tyr Pro
145                 150                 155                 160
```

```
gaa gat ata aag tat att acg agg ata atc atg ggg aaa ctc agg tta      528
Glu Asp Ile Lys Tyr Ile Thr Arg Ile Ile Met Gly Lys Leu Arg Leu
            165                 170                 175 ggc gtt gca gat tcc aca ata ctt gat tcc ctg gtg cat gca ttt ttc      576
Gly Val Ala Asp Ser Thr Ile Leu Asp Ser Leu Val His Ala Phe Phe
        180                 185                 190 tct aaa gat aat gcg gat atg gta gaa aca gct tac aat ttt cat cca      624
Ser Lys Asp Asn Ala Asp Met Val Glu Thr Ala Tyr Asn Phe His Pro
    195                 200                 205 gac ata ggg ctt ata gca acg ctc ctg cag aaa ggc gat ata aag gcc      672
Asp Ile Gly Leu Ile Ala Thr Leu Leu Gln Lys Gly Asp Ile Lys Ala
210                 215                 220 ata agc aac ata ggc cct gag cca ttg att cca ttc aag gta atg ctt      720
Ile Ser Asn Ile Gly Pro Glu Pro Leu Ile Pro Phe Lys Val Met Leu
225                 230                 235                 240 gca gaa agg ctg agg tcc atc gat gat ata agg gaa aaa atg aac cac      768
Ala Glu Arg Leu Arg Ser Ile Asp Asp Ile Arg Glu Lys Met Asn His
                245                 250                 255 cac gta tca ttt gag tat aaa tat gat ggg ctc agg aca gag ttg cac      816
His Val Ser Phe Glu Tyr Lys Tyr Asp Gly Leu Arg Thr Glu Leu His
            260                 265                 270 aaa aaa ggg gat aaa att aag att ttt tca aga ggg ctt gag gaa aca      864
Lys Lys Gly Asp Lys Ile Lys Ile Phe Ser Arg Gly Leu Glu Glu Thr
        275                 280                 285 act gaa aat ttc ccg gat att ata gaa aat ttc aaa aag agc tat tca      912
Thr Glu Asn Phe Pro Asp Ile Ile Glu Asn Phe Lys Lys Ser Tyr Ser
    290                 295                 300 ttt gaa tcc ata ata att gat gga gaa tcg gtt ccg ttt aat ccc gat      960
Phe Glu Ser Ile Ile Ile Asp Gly Glu Ser Val Pro Phe Asn Pro Asp
305                 310                 315                 320 aca ggg gaa ttg ttc cca ttc cag atg gtt tcc aaa agg agg gga aga     1008
Thr Gly Glu Leu Phe Pro Phe Gln Met Val Ser Lys Arg Arg Gly Arg
                325                 330                 335 aaa tat cag att aca gaa aaa tcc act gaa ata ccc ctt gtt atg ttt     1056
Lys Tyr Gln Ile Thr Glu Lys Ser Thr Glu Ile Pro Leu Val Met Phe
            340                 345                 350 att ttt gat ata ctt gag ctc aat gga agg ata ctt gtt aac ctc cca     1104
Ile Phe Asp Ile Leu Glu Leu Asn Gly Arg Ile Leu Val Asn Leu Pro
        355                 360                 365 tac gaa gaa agg cgt aaa att ctt gaa gaa aat ttt gta gat aat gag     1152
Tyr Glu Glu Arg Arg Lys Ile Leu Glu Glu Asn Phe Val Asp Asn Glu
    370                 375                 380 cac ttt agg ctg gca aca aga ttg tcc tcg gat gat tct gaa gag att     1200
His Phe Arg Leu Ala Thr Arg Leu Ser Ser Asp Asp Ser Glu Glu Ile
385                 390                 395                 400 aac aaa ttc ttt gaa cag agc ata gag gat ggg tgt gaa ggc att gtt     1248
Asn Lys Phe Phe Glu Gln Ser Ile Glu Asp Gly Cys Glu Gly Ile Val
                405                 410                 415 gcg aag gat aca tct gat gaa tct gtt tac cgt gca ggg gct cgt ggg     1296
Ala Lys Asp Thr Ser Asp Glu Ser Val Tyr Arg Ala Gly Ala Arg Gly
            420                 425                 430 tgg ctt tgg ata aaa ttt aaa agg gat tat cag aaa gaa ctt gcg gat     1344
Trp Leu Trp Ile Lys Phe Lys Arg Asp Tyr Gln Lys Glu Leu Ala Asp
        435                 440                 445 tcc atg gac ctg gta att atc ggt gca ttt aat ggc gtt gga agg agg     1392
Ser Met Asp Leu Val Ile Ile Gly Ala Phe Asn Gly Val Gly Arg Arg
    450                 455                 460 gca ggg gca tac ggt gca ctc ctc atg gca tca tat aac gaa gaa aca     1440
Ala Gly Ala Tyr Gly Ala Leu Leu Met Ala Ser Tyr Asn Glu Glu Thr
465                 470                 475                 480
```

```
cat gca ttc gag tca gtc aca aaa ctg gga aca gga ttc agt gat gag    1488
His Ala Phe Glu Ser Val Thr Lys Leu Gly Thr Gly Phe Ser Asp Glu
                485                 490                 495 gta tta ttt tca ttg cca aaa atg ctc tct gat ctt gta aga gac cac    1536
Val Leu Phe Ser Leu Pro Lys Met Leu Ser Asp Leu Val Arg Asp His
            500                 505                 510 aaa cct gct atg gtt gaa tca aaa atg gtt cct gac atc tgg ata tat    1584
Lys Pro Ala Met Val Glu Ser Lys Met Val Pro Asp Ile Trp Ile Tyr
        515                 520                 525 cca cag ata gtt atg gaa atc cag gga gca gaa att act gta agc cct    1632
Pro Gln Ile Val Met Glu Ile Gln Gly Ala Glu Ile Thr Val Ser Pro
    530                 535                 540 ata cat aca tgt gct ttt gga aaa ata gag aaa gat tcc ggc cct gcg    1680
Ile His Thr Cys Ala Phe Gly Lys Ile Glu Lys Asp Ser Gly Pro Ala
545                 550                 555                 560 tta aga ttt ccc aga tta att aaa ata cgt gac gat aaa aac gct gaa    1728
Leu Arg Phe Pro Arg Leu Ile Lys Ile Arg Asp Asp Lys Asn Ala Glu
                565                 570                 575 gac gct aca act acc aat gaa att ata gaa ctt tat aaa atg cag aaa    1776
Asp Ala Thr Thr Thr Asn Glu Ile Ile Glu Leu Tyr Lys Met Gln Lys
            580                 585                 590 aaa aca aaa taa                                                     1788
Lys Thr Lys
        595

<210> SEQ ID NO 2
<211> LENGTH: 595
<212> TYPE: PRT
<213> ORGANISM: Ferroplasma acidiphilum
<220> FEATURE:
<221> NAME/KEY: PEPTIDE
<222> LOCATION: (1)..(595)
<223> OTHER INFORMATION: Lig FA

<400> SEQUENCE: 2

Met Thr Lys Ser Tyr Asn Ile Leu Tyr Asp Tyr Tyr Leu Met Leu Phe
1               5                   10                  15

Ser Glu Ala Ser Lys Lys Phe Met Glu Met Glu Ser Thr Thr Lys Arg
            20                  25                  30

Leu Glu Leu Thr Ser Ile Leu Gly Ser Leu Leu Glu Asn Ala Gly Asp
        35                  40                  45

Asp Leu Lys Glu Leu Val Tyr Leu Ile Gln Gly Lys Leu Ala Pro Asp
    50                  55                  60

Tyr Glu Gly Ile Glu Phe Gly Val Ser Gly Lys Leu Ile Val Lys Ser
65                  70                  75                  80

Leu Ala Ala Ile Ser Gly Met Asp Glu Glu Val Asn Lys Leu Phe
                85                  90                  95

Tyr Lys Asn Gly Asp Leu Gly Ile Thr Ala Ser Glu Ile Arg Glu Lys
            100                 105                 110

Met Glu Gln Lys Pro Leu Phe Arg Glu Asp Leu Thr Val His Tyr Val
        115                 120                 125

Tyr Thr Arg Leu Met Glu Leu Ala Lys Ser Ala Gly His Gly Ser Val
    130                 135                 140

Lys Gly Lys Thr Asp Ile Tyr Ala Asp Leu Met Val Asn Ser Tyr Pro
145                 150                 155                 160

Glu Asp Ile Lys Tyr Ile Thr Arg Ile Ile Met Gly Lys Leu Arg Leu
                165                 170                 175

Gly Val Ala Asp Ser Thr Ile Leu Asp Ser Leu Val His Ala Phe Phe
            180                 185                 190
```

```
Ser Lys Asp Asn Ala Asp Met Val Glu Thr Ala Tyr Asn Phe His Pro
    195                 200                 205

Asp Ile Gly Leu Ile Ala Thr Leu Leu Gln Lys Gly Asp Ile Lys Ala
210                 215                 220

Ile Ser Asn Ile Gly Pro Glu Pro Leu Ile Pro Phe Lys Val Met Leu
225                 230                 235                 240

Ala Glu Arg Leu Arg Ser Ile Asp Asp Ile Arg Glu Lys Met Asn His
            245                 250                 255

His Val Ser Phe Glu Tyr Lys Tyr Asp Gly Leu Arg Thr Glu Leu His
            260                 265                 270

Lys Lys Gly Asp Lys Ile Lys Ile Phe Ser Arg Gly Leu Glu Glu Thr
        275                 280                 285

Thr Glu Asn Phe Pro Asp Ile Ile Glu Asn Phe Lys Lys Ser Tyr Ser
    290                 295                 300

Phe Glu Ser Ile Ile Ile Asp Gly Glu Ser Val Pro Phe Asn Pro Asp
305                 310                 315                 320

Thr Gly Glu Leu Phe Pro Phe Gln Met Val Ser Lys Arg Arg Gly Arg
                325                 330                 335

Lys Tyr Gln Ile Thr Glu Lys Ser Thr Glu Ile Pro Leu Val Met Phe
            340                 345                 350

Ile Phe Asp Ile Leu Glu Leu Asn Gly Arg Ile Leu Val Asn Leu Pro
        355                 360                 365

Tyr Glu Glu Arg Arg Lys Ile Leu Glu Glu Asn Phe Val Asp Asn Glu
    370                 375                 380

His Phe Arg Leu Ala Thr Arg Leu Ser Ser Asp Asp Ser Glu Glu Ile
385                 390                 395                 400

Asn Lys Phe Phe Glu Gln Ser Ile Glu Asp Gly Cys Glu Gly Ile Val
                405                 410                 415

Ala Lys Asp Thr Ser Asp Glu Ser Val Tyr Arg Ala Gly Ala Arg Gly
            420                 425                 430

Trp Leu Trp Ile Lys Phe Lys Arg Asp Tyr Gln Lys Glu Leu Ala Asp
        435                 440                 445

Ser Met Asp Leu Val Ile Gly Ala Phe Asn Gly Arg Gly Arg Arg
    450                 455                 460

Ala Gly Ala Tyr Gly Ala Leu Leu Met Ala Ser Tyr Asn Glu Glu Thr
465                 470                 475                 480

His Ala Phe Glu Ser Val Thr Lys Leu Gly Thr Gly Phe Ser Asp Glu
                485                 490                 495

Val Leu Phe Ser Leu Pro Lys Met Leu Ser Asp Leu Val Arg Asp His
            500                 505                 510

Lys Pro Ala Met Val Glu Ser Lys Met Val Pro Asp Ile Trp Ile Tyr
        515                 520                 525

Pro Gln Ile Val Met Glu Ile Gln Gly Ala Glu Ile Thr Val Ser Pro
    530                 535                 540

Ile His Thr Cys Ala Phe Gly Lys Ile Glu Lys Asp Ser Gly Pro Ala
545                 550                 555                 560

Leu Arg Phe Pro Arg Leu Ile Lys Ile Arg Asp Asp Lys Asn Ala Glu
                565                 570                 575

Asp Ala Thr Thr Thr Asn Glu Ile Ile Glu Leu Tyr Lys Met Gln Lys
            580                 585                 590

Lys Thr Lys
    595

<210> SEQ ID NO 3
```

-continued

```
<211> LENGTH: 927
<212> TYPE: DNA
<213> ORGANISM: Ferroplasma acidiphilum
<220> FEATURE:
<221> NAME/KEY: CDS
<222> LOCATION: (1)..(927)
<223> OTHER INFORMATION: est FA

<400> SEQUENCE: 3 atg cat tta atg aat atg gta gat ccg gat ttt aat tcg ctt ata gaa        48
Met His Leu Met Asn Met Val Asp Pro Asp Phe Asn Ser Leu Ile Glu
1               5                   10                  15 ttg tca aaa agt gcg gga gat atg acg aaa ata gag cct gct atg ctt        96
Leu Ser Lys Ser Ala Gly Asp Met Thr Lys Ile Glu Pro Ala Met Leu
            20                  25                  30 aga aat ttc ctt gac gaa tcc tca ctg agc tcc agg ggg gcg cca gtg       144
Arg Asn Phe Leu Asp Glu Ser Ser Leu Ser Ser Arg Gly Ala Pro Val
        35                  40                  45 gag ata aaa gag atc aaa gat tat aaa ata aaa ctg gat ggg cgc aca       192
Glu Ile Lys Glu Ile Lys Asp Tyr Lys Ile Lys Leu Asp Gly Arg Thr
    50                  55                  60 ctg aat gcc aga atg tat gat gat aat aat gca aaa tca gct att tta       240
Leu Asn Ala Arg Met Tyr Asp Asp Asn Asn Ala Lys Ser Ala Ile Leu
65                  70                  75                  80 tat tac cat ggt gga ggc ttt ctt ttc ggc aat att gaa aca tat gat       288
Tyr Tyr His Gly Gly Gly Phe Leu Phe Gly Asn Ile Glu Thr Tyr Asp
                85                  90                  95 aat tat tgc cgc ttc ctt gct aag gag tca ggg gtt aag att ata tct       336
Asn Tyr Cys Arg Phe Leu Ala Lys Glu Ser Gly Val Lys Ile Ile Ser
            100                 105                 110 att gaa tac cga ctg gca ccg gaa cat aaa ttt cca gat gct ttc aat       384
Ile Glu Tyr Arg Leu Ala Pro Glu His Lys Phe Pro Asp Ala Phe Asn
        115                 120                 125 gat gct tat gat tcg ttc cat tat ata gct aaa aag aag aaa gat ttt       432
Asp Ala Tyr Asp Ser Phe His Tyr Ile Ala Lys Lys Lys Lys Asp Phe
    130                 135                 140 gga ata gaa ggc aga ata ggc gta gcc ggt gat agt gcc ggt gca aat       480
Gly Ile Glu Gly Arg Ile Gly Val Ala Gly Asp Ser Ala Gly Ala Asn
145                 150                 155                 160 ctt gca gct gca tta tgc ctg aaa tgc cgt gat ggg aaa act gaa atg       528
Leu Ala Ala Ala Leu Cys Leu Lys Cys Arg Asp Gly Lys Thr Glu Met
                165                 170                 175 cct gct gta cag gta ttg ttc tat cca agc ctt gca ccg gat aat ttc       576
Pro Ala Val Gln Val Leu Phe Tyr Pro Ser Leu Ala Pro Asp Asn Phe
            180                 185                 190 tcc aga tct ttt att gag tat tcc gat aac tat gtc tta acg gga aag       624
Ser Arg Ser Phe Ile Glu Tyr Ser Asp Asn Tyr Val Leu Thr Gly Lys
        195                 200                 205 atg ata aga tat ttc gga aat atg tat tca aaa aat atg cag gat ctg       672
Met Ile Arg Tyr Phe Gly Asn Met Tyr Ser Lys Asn Met Gln Asp Leu
    210                 215                 220 ata aat cca tat ttc tcg ccc ctt gtt gcc gat gat ttt tca aat ctt       720
Ile Asn Pro Tyr Phe Ser Pro Leu Val Ala Asp Asp Phe Ser Asn Leu
225                 230                 235                 240 cca cca gcc ata atg gta act aat gaa tac gac cct ttg aga gac cct       768
Pro Pro Ala Ile Met Val Thr Asn Glu Tyr Asp Pro Leu Arg Asp Pro
                245                 250                 255 gaa gaa aca tat gtt aaa aaa ctc agg gaa gcg gga gtc agg gca gtt       816
Glu Glu Thr Tyr Val Lys Lys Leu Arg Glu Ala Gly Val Arg Ala Val
            260                 265                 270 gga ata agg ggg ata gga atg att cat ggc tcg gcc act gac ttt gag       864
Gly Ile Arg Gly Ile Gly Met Ile His Gly Ser Ala Thr Asp Phe Glu
```

```
                275                 280                 285
gtt tct gat ggt gcc aga aac att gta aaa atg gtt gcc agg att att    912
Val Ser Asp Gly Ala Arg Asn Ile Val Lys Met Val Ala Arg Ile Ile
    290                 295                 300 cct gac tat tta tag                                                927
Pro Asp Tyr Leu
305
```

<210> SEQ ID NO 4
<211> LENGTH: 308
<212> TYPE: PRT
<213> ORGANISM: Ferroplasma acidiphilum
<220> FEATURE:
<221> NAME/KEY: PEPTIDE
<222> LOCATION: (1)..(308)
<223> OTHER INFORMATION: Est FA

<400> SEQUENCE: 4

```
Met His Leu Met Asn Met Val Asp Pro Asp Phe Asn Ser Leu Ile Glu
1               5                   10                  15

Leu Ser Lys Ser Ala Gly Asp Met Thr Lys Ile Glu Pro Ala Met Leu
            20                  25                  30

Arg Asn Phe Leu Asp Glu Ser Ser Leu Ser Ser Arg Gly Ala Pro Val
        35                  40                  45

Glu Ile Lys Glu Ile Lys Asp Tyr Lys Ile Lys Leu Asp Gly Arg Thr
    50                  55                  60

Leu Asn Ala Arg Met Tyr Asp Asp Asn Asn Ala Lys Ser Ala Ile Leu
65                  70                  75                  80

Tyr Tyr His Gly Gly Gly Phe Leu Phe Gly Asn Ile Glu Thr Tyr Asp
                85                  90                  95

Asn Tyr Cys Arg Phe Leu Ala Lys Glu Ser Gly Val Lys Ile Ile Ser
            100                 105                 110

Ile Glu Tyr Arg Leu Ala Pro Glu His Lys Phe Pro Asp Ala Phe Asn
        115                 120                 125

Asp Ala Tyr Asp Ser Phe His Tyr Ile Ala Lys Lys Lys Asp Phe
    130                 135                 140

Gly Ile Glu Gly Arg Ile Gly Val Ala Gly Asp Ser Ala Gly Ala Asn
145                 150                 155                 160

Leu Ala Ala Ala Leu Cys Leu Lys Cys Arg Asp Gly Lys Thr Glu Met
                165                 170                 175

Pro Ala Val Gln Val Leu Phe Tyr Pro Ser Leu Ala Pro Asp Asn Phe
            180                 185                 190

Ser Arg Ser Phe Ile Glu Tyr Ser Asp Asn Tyr Val Leu Thr Gly Lys
        195                 200                 205

Met Ile Arg Tyr Phe Gly Asn Met Tyr Ser Lys Asn Met Gln Asp Leu
    210                 215                 220

Ile Asn Pro Tyr Phe Ser Pro Leu Val Ala Asp Asp Phe Ser Asn Leu
225                 230                 235                 240

Pro Pro Ala Ile Met Val Thr Asn Glu Tyr Asp Pro Leu Arg Asp Pro
                245                 250                 255

Glu Glu Thr Tyr Val Lys Lys Leu Arg Glu Ala Gly Val Arg Ala Val
            260                 265                 270

Gly Ile Arg Gly Ile Gly Met Ile His Gly Ser Ala Thr Asp Phe Glu
        275                 280                 285

Val Ser Asp Gly Ala Arg Asn Ile Val Lys Met Val Ala Arg Ile Ile
    290                 295                 300

Pro Asp Tyr Leu
```

-continued

305

<210> SEQ ID NO 5
<211> LENGTH: 2100
<212> TYPE: DNA
<213> ORGANISM: Ferroplasma acidiphilum
<220> FEATURE:
<221> NAME/KEY: CDS
<222> LOCATION: (339)..(1934)
<223> OTHER INFORMATION: alpha glu FA

<400> SEQUENCE: 5

```
tcccagtgca tttgcaacgt atgcaaaatt ccctgcagta cctgcaaatt tctctctaag      60
ggcctttaca ccggtagcct ggcctggaga cggtagagat ggcacagata gggttacatc     120
tatatttaag tggccaaaga aagccaaaaa cttcatagct agcgattgta attaaatatt     180
taacaaattt gaccgggaaa aggaatattt cctatcaact ggagccggca tctatatttc     240
ccacagcaat ttattttata ttgcttaatt attatcacat agaaataata tataatacat     300
tacatacttt cactatttca aacatttat attggtaa att aac tca tta tat ata      356
                                         Ile Asn Ser Leu Tyr Ile
                                          1               5 ttg aat cat aaa gtt ata att gcc gtt gca gtt agt gca att ctt att      404
Leu Asn His Lys Val Ile Ile Ala Val Ala Val Ser Ala Ile Leu Ile
         10                  15                  20 gca atg gtc ttt gca ggt gca aat att ccc tat ccg ggt tac aat cca      452
Ala Met Val Phe Ala Gly Ala Asn Ile Pro Tyr Pro Gly Tyr Asn Pro
                 25                  30                  35 acc gat cat ctc ata tct gga aaa cac cct att tcc aat gta tca gag      500
Thr Asp His Leu Ile Ser Gly Lys His Pro Ile Ser Asn Val Ser Glu
     40                  45                  50 gta ccc aag aat ttt act tta tct gga aac gta tct aat tct aat aat      548
Val Pro Lys Asn Phe Thr Leu Ser Gly Asn Val Ser Asn Ser Asn Asn
 55                  60                  65                  70 aat ttg cca ctt tcc gga act ata aca gta agc aat tcc aca atg tcc      596
Asn Leu Pro Leu Ser Gly Thr Ile Thr Val Ser Asn Ser Thr Met Ser
                 75                  80                  85 aga aca ttt aat acc agc agc aat gga agc tat aat atc act ctc ccg      644
Arg Thr Phe Asn Thr Ser Ser Asn Gly Ser Tyr Asn Ile Thr Leu Pro
                 90                  95                 100 caa ggg aat tat agt ata tcg tct tca ata cct gga ttt caa aat tat      692
Gln Gly Asn Tyr Ser Ile Ser Ser Ser Ile Pro Gly Phe Gln Asn Tyr
            105                 110                 115 tca tcc aca atc aat ctg gat agc aat aaa acg cag aat ata tca acg      740
Ser Ser Thr Ile Asn Leu Asp Ser Asn Lys Thr Gln Asn Ile Ser Thr
        120                 125                 130 cct cct gct act acc ata gga aat gga att aat cag gtt cca ggt tct      788
Pro Pro Ala Thr Thr Ile Gly Asn Gly Ile Asn Gln Val Pro Gly Ser
135                 140                 145                 150 acc aat gtg tca aca ctg gtt cca tat ctc aat aat agt att atg tct      836
Thr Asn Val Ser Thr Leu Val Pro Tyr Leu Asn Asn Ser Ile Met Ser
                155                 160                 165 gga ggg ctt aat act gac aat ata acc gga aca ttt gat aaa aat atc      884
Gly Gly Leu Asn Thr Asp Asn Ile Thr Gly Thr Phe Asp Lys Asn Ile
            170                 175                 180 aca ata gat ctg ggc aag aaa tta aac aat aca caa ttt gtt gta ttg      932
Thr Ile Asp Leu Gly Lys Lys Leu Asn Asn Thr Gln Phe Val Val Leu
        185                 190                 195 atg aag tta gac ggt gca gta tat agc tat aat tgg gtg aca aac gga      980
Met Lys Leu Asp Gly Ala Val Tyr Ser Tyr Asn Trp Val Thr Asn Gly
    200                 205                 210
```

```
agc ggg atg gcg aaa tta ttc ctt aaa tat tcc gga aat tat aca atg      1028
Ser Gly Met Ala Lys Leu Phe Leu Lys Tyr Ser Gly Asn Tyr Thr Met
215             220                 225                 230 tcc gca tat aca ctg tat tat aat tct agt gta att cat tac aat act      1076
Ser Ala Tyr Thr Leu Tyr Tyr Asn Ser Ser Val Ile His Tyr Asn Thr
                235                 240                 245 gca aat aat gat act gcc aga ttc aat atg aca gag cgt ata aca ttc      1124
Ala Asn Asn Asp Thr Ala Arg Phe Asn Met Thr Glu Arg Ile Thr Phe
            250                 255                 260 att tcc tct gtt att ctt caa agt gca gtc cca tta cat gat aat tca      1172
Ile Ser Ser Val Ile Leu Gln Ser Ala Val Pro Leu His Asp Asn Ser
        265                 270                 275 tca gtt gca aac tca aca ctc aca gtc aaa ggg gga gtt ttc tct gta      1220
Ser Val Ala Asn Ser Thr Leu Thr Val Lys Gly Gly Val Phe Ser Val
    280                 285                 290 cct tcc tta tcc gtt aac agt aat tta aca ggg act tac tat aaa tat      1268
Pro Ser Leu Ser Val Asn Ser Asn Leu Thr Gly Thr Tyr Tyr Lys Tyr
295                 300                 305                 310 gag gta ccc gtt ggt ttc tat aat ttt gct tac agt aat gcc cat tac      1316
Glu Val Pro Val Gly Phe Tyr Asn Phe Ala Tyr Ser Asn Ala His Tyr
                315                 320                 325 gtt tca aaa aat ttt ggc gtt gat gta aca gga aac agt aca gta aat      1364
Val Ser Lys Asn Phe Gly Val Asp Val Thr Gly Asn Ser Thr Val Asn
                330                 335                 340 aaa aca att gac cct tat tta ata tcc ata aat ata agg aat aat acc      1412
Lys Thr Ile Asp Pro Tyr Leu Ile Ser Ile Asn Ile Arg Asn Asn Thr
            345                 350                 355 ggg aat aca ttt aat tat aca ctt ggt agc aca ttt tat agt ggt aat      1460
Gly Asn Thr Phe Asn Tyr Thr Leu Gly Ser Thr Phe Tyr Ser Gly Asn
        360                 365                 370 ggc ata cac atg gct act tca ggc ata acc acc cta tta gtg ttc cat      1508
Gly Ile His Met Ala Thr Ser Gly Ile Thr Thr Leu Leu Val Phe His
375                 380                 385                 390 gac ggt aaa ata gta tac gac aat aca ata ctc cta acc agt gca aat      1556
Asp Gly Lys Ile Val Tyr Asp Asn Thr Ile Leu Leu Thr Ser Ala Asn
                395                 400                 405 cca tac tac cag ctt aac ctt act att agc aac aaa aat ctt aca ttt      1604
Pro Tyr Tyr Gln Leu Asn Leu Thr Ile Ser Asn Lys Asn Leu Thr Phe
                410                 415                 420 aac ggc att gaa acg gat tcg aca aat ctt tcc att gta tat tca ggc      1652
Asn Gly Ile Glu Thr Asp Ser Thr Asn Leu Ser Ile Val Tyr Ser Gly
            425                 430                 435 aat gta act tct aac ttt tat att gca tcc ctc gaa ttt gaa aac ttt      1700
Asn Val Thr Ser Asn Phe Tyr Ile Ala Ser Leu Glu Phe Glu Asn Phe
        440                 445                 450 agc aca tct gcc act aac gga atg ata att att tcc ggt gct gcg agt      1748
Ser Thr Ser Ala Thr Asn Gly Met Ile Ile Ile Ser Gly Ala Ala Ser
455                 460                 465                 470 gga agc tac ccc cta gac agt gga tta tat aca tac aat atg tca caa      1796
Gly Ser Tyr Pro Leu Asp Ser Gly Leu Tyr Thr Tyr Asn Met Ser Gln
                475                 480                 485 tcc ctt cca aca tca gcg ggc aac ctc aca ata aaa ctc gtt tat gat      1844
Ser Leu Pro Thr Ser Ala Gly Asn Leu Thr Ile Lys Leu Val Tyr Asp
            490                 495                 500 aat gat tct aag gta agc aca gat ggg cgt atg act gta gag gta tat      1892
Asn Asp Ser Lys Val Ser Thr Asp Gly Arg Met Thr Val Glu Val Tyr
        505                 510                 515 ggt tat aat ata tcc aca cta gga aat tat att acg gag tga              1934
Gly Tyr Asn Ile Ser Thr Leu Gly Asn Tyr Ile Thr Glu
520                 525                 530
```

```
tttttattgc tattcaaaaa gaatgtacag aaaacagaga aaattgaaga gaagactaaa      1994
actgtgttga aaataaaaac agttgacgat atacctgtaa taaggaaat gaggaagaag       2054 ataggaatg gggaacgaaa ggaagcaata atatacgggt acacaa                      2100
```

<210> SEQ ID NO 6
<211> LENGTH: 531
<212> TYPE: PRT
<213> ORGANISM: Ferroplasma acidiphilum
<220> FEATURE:
<221> NAME/KEY: PEPTIDE
<222> LOCATION: (1)..(531)
<223> OTHER INFORMATION: alpha Glu FA

<400> SEQUENCE: 6

```
Ile Asn Ser Leu Tyr Ile Leu Asn His Lys Val Ile Ala Val Ala
1               5                   10                  15

Val Ser Ala Ile Leu Ile Ala Met Val Phe Ala Gly Ala Asn Ile Pro
            20                  25                  30

Tyr Pro Gly Tyr Asn Pro Thr Asp His Leu Ile Ser Gly Lys His Pro
        35                  40                  45

Ile Ser Asn Val Ser Glu Val Pro Lys Asn Phe Thr Leu Ser Gly Asn
50                  55                  60

Val Ser Asn Ser Asn Asn Asn Leu Pro Leu Ser Gly Thr Ile Thr Val
65                  70                  75                  80

Ser Asn Ser Thr Met Ser Arg Thr Phe Asn Thr Ser Asn Gly Ser
                85                  90                  95

Tyr Asn Ile Thr Leu Pro Gln Gly Asn Tyr Ser Ile Ser Ser Ile
            100                 105                 110

Pro Gly Phe Gln Asn Tyr Ser Ser Thr Ile Asn Leu Asp Ser Asn Lys
        115                 120                 125

Thr Gln Asn Ile Ser Thr Pro Pro Ala Thr Thr Ile Gly Asn Gly Ile
130                 135                 140

Asn Gln Val Pro Gly Ser Thr Asn Val Ser Thr Leu Val Pro Tyr Leu
145                 150                 155                 160

Asn Asn Ser Ile Met Ser Gly Gly Leu Asn Thr Asp Asn Ile Thr Gly
                165                 170                 175

Thr Phe Asp Lys Asn Ile Thr Ile Asp Leu Gly Lys Lys Leu Asn Asn
            180                 185                 190

Thr Gln Phe Val Val Leu Met Lys Leu Asp Gly Ala Val Tyr Ser Tyr
        195                 200                 205

Asn Trp Val Thr Asn Gly Ser Gly Met Ala Lys Leu Phe Leu Lys Tyr
210                 215                 220

Ser Gly Asn Tyr Thr Met Ser Ala Tyr Thr Leu Tyr Tyr Asn Ser Ser
225                 230                 235                 240

Val Ile His Tyr Asn Thr Ala Asn Asn Asp Thr Ala Arg Phe Asn Met
                245                 250                 255

Thr Glu Arg Ile Thr Phe Ile Ser Ser Val Ile Leu Gln Ser Ala Val
            260                 265                 270

Pro Leu His Asp Asn Ser Ser Val Ala Asn Ser Thr Leu Thr Val Lys
        275                 280                 285

Gly Gly Val Phe Ser Val Pro Ser Leu Ser Val Asn Ser Asn Leu Thr
290                 295                 300

Gly Thr Tyr Tyr Lys Tyr Glu Val Pro Val Gly Phe Tyr Asn Phe Ala
305                 310                 315                 320

Tyr Ser Asn Ala His Tyr Val Ser Lys Asn Phe Gly Val Asp Val Thr
                325                 330                 335
```

-continued

```
Gly Asn Ser Thr Val Asn Lys Thr Ile Asp Pro Tyr Leu Ile Ser Ile
            340                 345                 350
Asn Ile Arg Asn Asn Thr Gly Asn Thr Phe Asn Tyr Thr Leu Gly Ser
        355                 360                 365
Thr Phe Tyr Ser Gly Asn Gly Ile His Met Ala Thr Ser Gly Ile Thr
    370                 375                 380
Thr Leu Leu Val Phe His Asp Gly Lys Ile Val Tyr Asp Asn Thr Ile
385                 390                 395                 400
Leu Leu Thr Ser Ala Asn Pro Tyr Tyr Gln Leu Asn Leu Thr Ile Ser
                405                 410                 415
Asn Lys Asn Leu Thr Phe Asn Gly Ile Glu Thr Asp Ser Thr Asn Leu
            420                 425                 430
Ser Ile Val Tyr Ser Gly Asn Val Thr Ser Asn Phe Tyr Ile Ala Ser
        435                 440                 445
Leu Glu Phe Glu Asn Phe Ser Thr Ser Ala Thr Asn Gly Met Ile Ile
    450                 455                 460
Ile Ser Gly Ala Ala Ser Gly Ser Tyr Pro Leu Asp Ser Gly Leu Tyr
465                 470                 475                 480
Thr Tyr Asn Met Ser Gln Ser Leu Pro Thr Ser Ala Gly Asn Leu Thr
                485                 490                 495
Ile Lys Leu Val Tyr Asp Asn Asp Ser Lys Val Ser Thr Asp Gly Arg
            500                 505                 510
Met Thr Val Glu Val Tyr Gly Tyr Asn Ile Ser Thr Leu Gly Asn Tyr
        515                 520                 525
Ile Thr Glu
    530

<210> SEQ ID NO 7
<211> LENGTH: 1550
<212> TYPE: DNA
<213> ORGANISM: Ferroplasma acidiphilum
<220> FEATURE:
<221> NAME/KEY: CDS
<222> LOCATION: (621)..(1361)
<223> OTHER INFORMATION: glu FA

<400> SEQUENCE: 7
accccactcc tttcacttaa tatcttggta tagtttttg aaaatatagc attatacatg      60
taatcaaaat caattaaaat atcaagcttt tctttggaat aagcatcaat aatttcatca    120
taattgtatc tattaccatt cacttcatga aaatactttg taattttaat cccttgattc    180
tccaattcat gagcctttcg aatcaaaact tcttttttg atttattata tatctcggga    240
ctaggcaagt atacaatatt aaaataatta tttaatattt ttataatatt tattgtatga    300
gtttgtgccc ctccgtaact tgaaaaaatg tcaggaccgg ttacaccaat attcacgata    360
cttgtatcaa tttcgtatta ataatatttc tcaaaataat gtttgagatg atgtttataa    420
tctagacaat ttaaatgaac agtaattcaa aaatttattt gataatcaag aaaataataa    480
cggtataaaa tacttttatc tgagattgct agaatccata atataacacc ataatcaaat    540
tatacagatt aagtcattca ggtaatggaa aactatgttt tactgagaag ctttatatta    600
taatattata tgctattaaa atg gaa att cag gat atc gat tta act att gtt   653
                       Met Glu Ile Gln Asp Ile Asp Leu Thr Ile Val
                        1               5                   10 tta gca act ctt aac gaa ata gat aat ctt cca cgg ctc tgt tct gat   701
Leu Ala Thr Leu Asn Glu Ile Asp Asn Leu Pro Arg Leu Cys Ser Asp
        15                  20                  25
```

| | | |
|---|---|---|
| atc gat tca ata tta aaa aat acg aaa ata aag tat cag tta tta ttt<br>Ile Asp Ser Ile Leu Lys Asn Thr Lys Ile Lys Tyr Gln Leu Leu Phe<br>        30                        35                        40 | 749 | |
| gtc gat gat aac agt agc gat gga acc aga gag ttt att ata gag tat<br>Val Asp Asp Asn Ser Ser Asp Gly Thr Arg Glu Phe Ile Ile Glu Tyr<br>45                         50                         55 | 797 | |
| tgc aat aaa aat aaa tta tca aaa tat att ttt aat gaa tac aag aaa<br>Cys Asn Lys Asn Lys Leu Ser Lys Tyr Ile Phe Asn Glu Tyr Lys Lys<br>60                         65                      70                      75 | 845 | |
| tca acc ctt ata gcc aga tac cag gga ata aac aat gca gat ggg aaa<br>Ser Thr Leu Ile Ala Arg Tyr Gln Gly Ile Asn Asn Ala Asp Gly Lys<br>                     80                        85                        90 | 893 | |
| tat att ata ctt atg gat tca gat ttg caa cat ccc cca aaa tat ctc<br>Tyr Ile Ile Leu Met Asp Ser Asp Leu Gln His Pro Pro Lys Tyr Leu<br>              95                              100                      105 | 941 | |
| tta aat ata tat aac agt tta ttg aaa cat aat gat atc gta att gcc<br>Leu Asn Ile Tyr Asn Ser Leu Leu Lys His Asn Asp Ile Val Ile Ala<br>           110                         115                      120 | 989 | |
| agc aga tac gtt aaa ggt ggc agt acc gga aat cgc aaa cct ata cgt<br>Ser Arg Tyr Val Lys Gly Gly Ser Thr Gly Asn Arg Lys Pro Ile Arg<br>       125                         130                      135 | 1037 | |
| ggc att ata tca cgt ggg gca tct ttg atg gca caa cta cta ttg aaa<br>Gly Ile Ile Ser Arg Gly Ala Ser Leu Met Ala Gln Leu Leu Leu Lys<br>140                      145                      150                      155 | 1085 | |
| agc agc agg cag ata aag gac ccc ata tcg tgt tat att ggc ttt aga<br>Ser Ser Arg Gln Ile Lys Asp Pro Ile Ser Cys Tyr Ile Gly Phe Arg<br>                160                      165                      170 | 1133 | |
| aaa ggg ctg aaa ttg gat ata gac gaa ggc tgg aga ggc tat gag ata<br>Lys Gly Leu Lys Leu Asp Ile Asp Glu Gly Trp Arg Gly Tyr Glu Ile<br>           175                         180                      185 | 1181 | |
| ggt att ttc tta agg gct agc aat aat aat gtt aag gta aag gaa ata<br>Gly Ile Phe Leu Arg Ala Ser Asn Asn Asn Val Lys Val Lys Glu Ile<br>190                      195                      200 | 1229 | |
| cct tat cga ttt gcg gaa agg gaa aat gga aaa tca aaa gta acg tcc<br>Pro Tyr Arg Phe Ala Glu Arg Glu Asn Gly Lys Ser Lys Val Thr Ser<br>       205                         210                      215 | 1277 | |
| agt gta aaa ttt tta aga gtt tat ata ata gaa tta tta ttg gca aaa<br>Ser Val Lys Phe Leu Arg Val Tyr Ile Ile Glu Leu Leu Leu Ala Lys<br>220                      225                      230                      235 | 1325 | |
| aga gtt gag ata aga aat tat aaa cca att ttg tga tgtatataat<br>Arg Val Glu Ile Arg Asn Tyr Lys Pro Ile Leu<br>           240                          245 | 1371 | |
| ataagttaa attgtagtaa tggcattgta ttcatttgag attattgttt gttcttattg | 1431 | |
| aaccttaata taaataaaaa gaacgatata gcaatggcta tccctattat tttaaagtat | 1491 | |
| attaaatcta tactgattaa tctataataa tataatgtaa atagctgagt agaacacaa | 1550 | |

<210> SEQ ID NO 8
<211> LENGTH: 246
<212> TYPE: PRT
<213> ORGANISM: Ferroplasma acidiphilum
<220> FEATURE:
<221> NAME/KEY: PEPTIDE
<222> LOCATION: (1)..(246)
<223> OTHER INFORMATION: Glu FA

<400> SEQUENCE: 8

Met Glu Ile Gln Asp Ile Asp Leu Thr Ile Val Leu Ala Thr Leu Asn
1                 5                    10                    15

Glu Ile Asp Asn Leu Pro Arg Leu Cys Ser Asp Ile Asp Ser Ile Leu
                 20                    25                    30

```
Lys Asn Thr Lys Ile Lys Tyr Gln Leu Leu Phe Val Asp Asp Asn Ser
             35                  40                  45

Ser Asp Gly Thr Arg Glu Phe Ile Ile Glu Tyr Cys Asn Lys Asn Lys
 50                  55                  60

Leu Ser Lys Tyr Ile Phe Asn Glu Tyr Lys Lys Ser Thr Leu Ile Ala
 65                  70                  75                  80

Arg Tyr Gln Gly Ile Asn Asn Ala Asp Gly Lys Tyr Ile Ile Leu Met
                 85                  90                  95

Asp Ser Asp Leu Gln His Pro Pro Lys Tyr Leu Leu Asn Ile Tyr Asn
                100                 105                 110

Ser Leu Leu Lys His Asn Asp Ile Val Ile Ala Ser Arg Tyr Val Lys
            115                 120                 125

Gly Gly Ser Thr Gly Asn Arg Lys Pro Ile Arg Gly Ile Ile Ser Arg
130                 135                 140

Gly Ala Ser Leu Met Ala Gln Leu Leu Leu Lys Ser Ser Arg Gln Ile
145                 150                 155                 160

Lys Asp Pro Ile Ser Cys Tyr Ile Gly Phe Arg Lys Gly Leu Lys Leu
                165                 170                 175

Asp Ile Asp Glu Gly Trp Arg Gly Tyr Glu Ile Gly Ile Phe Leu Arg
            180                 185                 190

Ala Ser Asn Asn Asn Val Lys Val Lys Glu Ile Pro Tyr Arg Phe Ala
        195                 200                 205

Glu Arg Glu Asn Gly Lys Ser Lys Val Thr Ser Ser Val Lys Phe Leu
210                 215                 220

Arg Val Tyr Ile Ile Glu Leu Leu Leu Ala Lys Arg Val Glu Ile Arg
225                 230                 235                 240

Asn Tyr Lys Pro Ile Leu
                245

<210> SEQ ID NO 9
<211> LENGTH: 2000
<212> TYPE: DNA
<213> ORGANISM: Ferroplasma acidiphilum
<220> FEATURE:
<221> NAME/KEY: CDS
<222> LOCATION: (840)..(1985)
<223> OTHER INFORMATION: glu FA2

<400> SEQUENCE: 9
gatcgtatta catgatcgta atataatcca ctatagttta tttttcctgc ccatgcactc      60
cagtaatttc ttgtttcttc cagccgtgta tatgattcat attgccttac attgccaatt     120
tgccttactc cgcttaatac aacaatccat tcatgtgaac cttttccac ttttatcctg      180 ctgtatacat ttccatttcc ctttttcaat ttaagatttg tggaaattcc aagtgtgtca     240
tctgtacatg agaaaatata accatttcta tccctggtta tgtttgtttt ccctgagcca     300
aagttaaaat gcgattttat atctattgat acttcaacat cagaatatgg ggcctcaatt     360
agccggtgta tctccggaaa cgttattgtg ctatatgatg atgttggaag aaaatctgtg     420
agccttaaaa ttacctgatt gttatttaca aactctgtta taagtatatt ggttgattct     480
tcgtaatact ggttgacatt gctttccatt acagggctgg tcttgaaata accaccattt     540
ctggcatcaa gaatagaatc aaagacagga tttgaattaa agtgggcaa acatgcccag      600 tcaatagttc catctatacc aacaagtgct gcagtgcggt tatttgcaat aaaaccgtga     660
tttgcaatct ttaaataatc agatctgtat gcatcatgca gatcgtaaag ccctctgtat     720
gtacccatgg taaaattgat aataataata tataaagagt ttatcagaag ccagaaataa     780
```

```
                                                           -continued
tgctaaatgg taaaactgga aaataggaat agatttataa ccagacgtat tatattttt    839 atg aaa ata act tac cac aag cta aaa atg cca ctg ata agc cca ttc    887
Met Lys Ile Thr Tyr His Lys Leu Lys Met Pro Leu Ile Ser Pro Phe
1               5                  10                  15 aca acc agc ttc gga aca gat gta aac aag gat gtt tat gtt ttc aag    935
Thr Thr Ser Phe Gly Thr Asp Val Asn Lys Asp Val Tyr Val Phe Lys
            20                  25                  30 ctt gaa cat aat gga ata act gct tat tct gaa agt gtt acc gac gaa    983
Leu Glu His Asn Gly Ile Thr Ala Tyr Ser Glu Ser Val Thr Asp Glu
        35                  40                  45 aat cct ttt tat ggc tca gaa gat aat tat aca gta ttc cat att gta   1031
Asn Pro Phe Tyr Gly Ser Glu Asp Asn Tyr Thr Val Phe His Ile Val
    50                  55                  60 aaa cag tat ctt gca cca gta gta aaa ggc ctt cca gag ccg gat gaa   1079
Lys Gln Tyr Leu Ala Pro Val Val Lys Gly Leu Pro Glu Pro Asp Glu
65                  70                  75                  80 ttc aat gaa cag gta aaa ttt ata aaa ggc aat aat atg gca aaa gct   1127
Phe Asn Glu Gln Val Lys Phe Ile Lys Gly Asn Asn Met Ala Lys Ala
                85                  90                  95 tcc atg gaa atg ctt ctc tat gat tat tat gca aaa gca aat aaa aaa   1175
Ser Met Glu Met Leu Leu Tyr Asp Tyr Tyr Ala Lys Ala Asn Lys Lys
            100                 105                 110 tcc ctg gta gat tac ata ggg cac agc agg gga tat gca aac gtt gga   1223
Ser Leu Val Asp Tyr Ile Gly His Ser Arg Gly Tyr Ala Asn Val Gly
        115                 120                 125 ata tca ctt gga atg gat gat ata aac gtt aca tta aag aag ata cag   1271
Ile Ser Leu Gly Met Asp Asp Ile Asn Val Thr Leu Lys Lys Ile Gln
    130                 135                 140 gaa gcc ctt gac cgt gga tat aaa aga att aaa gtc aaa ata atg aag   1319
Glu Ala Leu Asp Arg Gly Tyr Lys Arg Ile Lys Val Lys Ile Met Lys
145                 150                 155                 160 gga aag gaa ata ggt ata cta agt gct gta agg gac aat ttt ccg gat   1367
Gly Lys Glu Ile Gly Ile Leu Ser Ala Val Arg Asp Asn Phe Pro Asp
                165                 170                 175 ata gtt tta agt gca gac gcc aac agc gat tat acc gag aag gat ttt   1415
Ile Val Leu Ser Ala Asp Ala Asn Ser Asp Tyr Thr Glu Lys Asp Phe
            180                 185                 190 gat ttg att aaa aaa ata gac aga tac aat ctt gta tat ctg gag cag   1463
Asp Leu Ile Lys Lys Ile Asp Arg Tyr Asn Leu Val Tyr Leu Glu Gln
        195                 200                 205 ccc ctg tac cat gat gat ata ata tac cat tca agg ctt gca aag gga   1511
Pro Leu Tyr His Asp Asp Ile Ile Tyr His Ser Arg Leu Ala Lys Gly
    210                 215                 220 tta tcc acg cca tta tgc ctg gat gaa tct att act tca ccg gag aag   1559
Leu Ser Thr Pro Leu Cys Leu Asp Glu Ser Ile Thr Ser Pro Glu Lys
225                 230                 235                 240 gca cag aaa gca ttt gaa atg ggt gcg tgt aag gtt ata aac ata aaa   1607
Ala Gln Lys Ala Phe Glu Met Gly Ala Cys Lys Val Ile Asn Ile Lys
                245                 250                 255 gag gga agg cta ggc gga atc gga aat tcc tta aaa gtt atg gga ata   1655
Glu Gly Arg Leu Gly Gly Ile Gly Asn Ser Leu Lys Val Met Gly Ile
            260                 265                 270 gtg aag gaa ttc aag ggc cat gta tgg att gga gga atg tta gaa act   1703
Val Lys Glu Phe Lys Gly His Val Trp Ile Gly Gly Met Leu Glu Thr
        275                 280                 285 gga atc gga agg tcc ttt aat gtt tcc atg gca tct ctt tct gat att   1751
Gly Ile Gly Arg Ser Phe Asn Val Ser Met Ala Ser Leu Ser Asp Ile
    290                 295                 300 aat tat cct gga gac aca tcg ccc aat gac aaa tac ttt aaa aat gac   1799
Asn Tyr Pro Gly Asp Thr Ser Pro Asn Asp Lys Tyr Phe Lys Asn Asp
```

```
                305                 310                 315                 320
ata gtt aag aat cca ttc aca atg gaa aat ggc aca att aag cct aat    1847
Ile Val Lys Asn Pro Phe Thr Met Glu Asn Gly Thr Ile Lys Pro Asn
            325                 330                 335 aag ggt aca ggc atc ggt gtt gaa atc agt gaa gag tat cta aaa aaa    1895
Lys Gly Thr Gly Ile Gly Val Glu Ile Ser Glu Glu Tyr Leu Lys Lys
        340                 345                 350 tat acc gtt gaa gag ggg ata ata gca tga ata atg tat tcc agt att    1943
Tyr Thr Val Glu Glu Gly Ile Ile Ala     Ile Met Tyr Ser Ser Ile
    355                 360                     365 tca aaa gcc agc agg att caa tgc tat cag att taa aat cat            1985
Ser Lys Ala Ser Arg Ile Gln Cys Tyr Gln Ile     Asn His
370                 375                             380 tagtagagat ggaaa                                                   2000

<210> SEQ ID NO 10
<211> LENGTH: 361
<212> TYPE: PRT
<213> ORGANISM: Ferroplasma acidiphilum
<220> FEATURE:
<221> NAME/KEY: PEPTIDE
<222> LOCATION: (1)..(361)
<223> OTHER INFORMATION: Glu FA2

<400> SEQUENCE: 10

Met Lys Ile Thr Tyr His Lys Leu Lys Met Pro Leu Ile Ser Pro Phe
1               5                   10                  15

Thr Thr Ser Phe Gly Thr Asp Val Asn Lys Asp Val Tyr Val Phe Lys
            20                  25                  30

Leu Glu His Asn Gly Ile Thr Ala Tyr Ser Glu Ser Val Thr Asp Glu
        35                  40                  45

Asn Pro Phe Tyr Gly Ser Glu Asp Asn Tyr Thr Val Phe His Ile Val
    50                  55                  60

Lys Gln Tyr Leu Ala Pro Val Val Lys Gly Leu Pro Glu Pro Asp Glu
65                  70                  75                  80

Phe Asn Glu Gln Val Lys Phe Ile Lys Gly Asn Asn Met Ala Lys Ala
                85                  90                  95

Ser Met Glu Met Leu Leu Tyr Asp Tyr Tyr Ala Lys Ala Asn Lys Lys
            100                 105                 110

Ser Leu Val Asp Tyr Ile Gly His Ser Arg Gly Tyr Ala Asn Val Gly
        115                 120                 125

Ile Ser Leu Gly Met Asp Asp Ile Asn Val Thr Leu Lys Lys Ile Gln
    130                 135                 140

Glu Ala Leu Asp Arg Gly Tyr Lys Arg Ile Lys Val Lys Ile Met Lys
145                 150                 155                 160

Gly Lys Glu Ile Gly Ile Leu Ser Ala Val Arg Asp Asn Phe Pro Asp
                165                 170                 175

Ile Val Leu Ser Ala Asp Ala Asn Ser Asp Tyr Thr Glu Lys Asp Phe
            180                 185                 190

Asp Leu Ile Lys Lys Ile Asp Arg Tyr Asn Leu Val Tyr Leu Glu Gln
        195                 200                 205

Pro Leu Tyr His Asp Asp Ile Ile Tyr His Ser Arg Leu Ala Lys Gly
    210                 215                 220

Leu Ser Thr Pro Leu Cys Leu Asp Glu Ser Ile Thr Ser Pro Glu Lys
225                 230                 235                 240

Ala Gln Lys Ala Phe Glu Met Gly Ala Cys Lys Val Ile Asn Ile Lys
                245                 250                 255
```

| | | | | | | | | | | | | |
|---|---|---|---|---|---|---|---|---|---|---|---|---|
| Glu | Gly | Arg | Leu | Gly | Gly | Ile | Gly | Asn | Ser | Leu | Lys | Val | Met | Gly | Ile |
| | | 260 | | | | 265 | | | | 270 | | |

Val Lys Glu Phe Lys Gly His Val Trp Ile Gly Gly Met Leu Glu Thr
           275                       280                       285

Gly Ile Gly Arg Ser Phe Asn Val Ser Met Ala Ser Leu Ser Asp Ile
    290                       295                       300

Asn Tyr Pro Gly Asp Thr Ser Pro Asn Asp Lys Tyr Phe Lys Asn Asp
305                       310                     315                  320

Ile Val Lys Asn Pro Phe Thr Met Glu Asn Gly Thr Ile Lys Pro Asn
           325                       330                       335

Lys Gly Thr Gly Ile Gly Val Glu Ile Ser Glu Glu Tyr Leu Lys Lys
        340                     345                     350

Tyr Thr Val Glu Glu Gly Ile Ile Ala
       355                     360

<210> SEQ ID NO 11
<211> LENGTH: 1596
<212> TYPE: DNA
<213> ORGANISM: Ferroplasma acidiphilum
<220> FEATURE:
<221> NAME/KEY: CDS
<222> LOCATION: (1)..(1596)
<223> OTHER INFORMATION: alpha glu FA, in Figure 11 designated sequence
    5a

<400> SEQUENCE: 11 att aac tca tta tat ata ttg aat cat aaa gtt ata att gcc gtt gca      48
Ile Asn Ser Leu Tyr Ile Leu Asn His Lys Val Ile Ile Ala Val Ala
1               5                  10                 15 gtt agt gca att ctt att gca atg gtc ttt gca ggt gca aat att ccc      96
Val Ser Ala Ile Leu Ile Ala Met Val Phe Ala Gly Ala Asn Ile Pro
           20                     25                 30 tat ccg ggt tac aat cca acc gat cat ctc ata tct gga aaa cac cct    144
Tyr Pro Gly Tyr Asn Pro Thr Asp His Leu Ile Ser Gly Lys His Pro
               35                  40                 45 att tcc aat gta tca gag gta ccc aag aat ttt act tta tct gga aac    192
Ile Ser Asn Val Ser Glu Val Pro Lys Asn Phe Thr Leu Ser Gly Asn
 50                   55                  60 gta tct aat tct aat aat aat ttg cca ctt tcc gga act ata aca gta    240
Val Ser Asn Ser Asn Asn Asn Leu Pro Leu Ser Gly Thr Ile Thr Val
65              70                  75                 80 agc aat tcc aca atg tcc aga aca ttt aat acc agc agc aat gga agc    288
Ser Asn Ser Thr Met Ser Arg Thr Phe Asn Thr Ser Ser Asn Gly Ser
                    85                  90                 95 tat aat atc act ctc ccg caa ggg aat tat agt ata tcg tct tca ata    336
Tyr Asn Ile Thr Leu Pro Gln Gly Asn Tyr Ser Ile Ser Ser Ser Ile
                 100                  105              110 cct gga ttt caa aat tat tca tcc aca atc aat ctg gat agc aat aaa    384
Pro Gly Phe Gln Asn Tyr Ser Ser Thr Ile Asn Leu Asp Ser Asn Lys
           115                  120               125 acg cag aat ata tca acg cct cct gct act acc ata gga aat gga att    432
Thr Gln Asn Ile Ser Thr Pro Pro Ala Thr Thr Ile Gly Asn Gly Ile
       130                  135               140 aat cag gtt cca ggt tct acc aat gtg tca aca ctg gtt cca tat ctc    480
Asn Gln Val Pro Gly Ser Thr Asn Val Ser Thr Leu Val Pro Tyr Leu
145              150                  155                 160 aat aat agt att atg tct gga ggg ctt aat act gac aat ata acc gga    528
Asn Asn Ser Ile Met Ser Gly Gly Leu Asn Thr Asp Asn Ile Thr Gly
                 165                  170              175 aca ttt gat aaa aat atc aca ata gat ctg ggc aag aaa tta aac aat    576
Thr Phe Asp Lys Asn Ile Thr Ile Asp Leu Gly Lys Lys Leu Asn Asn -continued

```
                180                 185                 190
aca caa ttt gtt gta ttg atg aag tta gac ggt gca gta tat agc tat       624
Thr Gln Phe Val Val Leu Met Lys Leu Asp Gly Ala Val Tyr Ser Tyr
        195                 200                 205 aat tgg gtg aca aac gga agc ggg atg gcg aaa tta ttc ctt aaa tat       672
Asn Trp Val Thr Asn Gly Ser Gly Met Ala Lys Leu Phe Leu Lys Tyr
    210                 215                 220 tcc gga aat tat aca atg tcc gca tat aca ctg tat tat aat tct agt       720
Ser Gly Asn Tyr Thr Met Ser Ala Tyr Thr Leu Tyr Tyr Asn Ser Ser
225                 230                 235                 240 gta att cat tac aat act gca aat aat gat act gcc aga ttc aat atg       768
Val Ile His Tyr Asn Thr Ala Asn Asn Asp Thr Ala Arg Phe Asn Met
        245                 250                 255 aca gag cgt ata aca ttc att tcc tct gtt att ctt caa agt gca gtc       816
Thr Glu Arg Ile Thr Phe Ile Ser Ser Val Ile Leu Gln Ser Ala Val
    260                 265                 270 cca tta cat gat aat tca tca gtt gca aac tca aca ctc aca gtc aaa       864
Pro Leu His Asp Asn Ser Ser Val Ala Asn Ser Thr Leu Thr Val Lys
275                 280                 285 ggg gga gtt ttc tct gta cct tcc tta tcc gtt aac agt aat tta aca       912
Gly Gly Val Phe Ser Val Pro Ser Leu Ser Val Asn Ser Asn Leu Thr
        290                 295                 300 ggg act tac tat aaa tat gag gta ccc gtt ggt ttc tat aat ttt gct       960
Gly Thr Tyr Tyr Lys Tyr Glu Val Pro Val Gly Phe Tyr Asn Phe Ala
305                 310                 315                 320 tac agt aat gcc cat tac gtt tca aaa aat ttt ggc gtt gat gta aca      1008
Tyr Ser Asn Ala His Tyr Val Ser Lys Asn Phe Gly Val Asp Val Thr
                325                 330                 335 gga aac agt aca gta aat aaa aca att gac cct tat tta ata tcc ata      1056
Gly Asn Ser Thr Val Asn Lys Thr Ile Asp Pro Tyr Leu Ile Ser Ile
            340                 345                 350 aat ata agg aat aat acc ggg aat aca ttt aat tat aca ctt ggt agc      1104
Asn Ile Arg Asn Asn Thr Gly Asn Thr Phe Asn Tyr Thr Leu Gly Ser
        355                 360                 365 aca ttt tat agt ggt aat ggc ata cac atg gct act tca ggc ata acc      1152
Thr Phe Tyr Ser Gly Asn Gly Ile His Met Ala Thr Ser Gly Ile Thr
370                 375                 380 acc cta tta gtg ttc cat gac ggt aaa ata gta tac gac aat aca ata      1200
Thr Leu Leu Val Phe His Asp Gly Lys Ile Val Tyr Asp Asn Thr Ile
385                 390                 395                 400 ctc cta acc agt gca aat cca tac tac cag ctt aac ctt act att agc      1248
Leu Leu Thr Ser Ala Asn Pro Tyr Tyr Gln Leu Asn Leu Thr Ile Ser
                405                 410                 415 aac aaa aat ctt aca ttt aac ggc att gaa acg gat tcg aca aat ctt      1296
Asn Lys Asn Leu Thr Phe Asn Gly Ile Glu Thr Asp Ser Thr Asn Leu
            420                 425                 430 tcc att gta tat tca ggc aat gta act tct aac ttt tat att gca tcc      1344
Ser Ile Val Tyr Ser Gly Asn Val Thr Ser Asn Phe Tyr Ile Ala Ser
        435                 440                 445 ctc gaa ttt gaa aac ttt agc aca tct gcc act aac gga atg ata att      1392
Leu Glu Phe Glu Asn Phe Ser Thr Ser Ala Thr Asn Gly Met Ile Ile
450                 455                 460 att tcc ggt gct gcg agt gga agc tac ccc cta gac agt gga tta tat      1440
Ile Ser Gly Ala Ala Ser Gly Ser Tyr Pro Leu Asp Ser Gly Leu Tyr
465                 470                 475                 480 aca tac aat atg tca caa tcc ctt cca aca tca gcg ggc aac ctc aca      1488
Thr Tyr Asn Met Ser Gln Ser Leu Pro Thr Ser Ala Gly Asn Leu Thr
                485                 490                 495 ata aaa ctc gtt tat gat aat gat tct aag gta agc aca gat ggg cgt      1536
Ile Lys Leu Val Tyr Asp Asn Asp Ser Lys Val Ser Thr Asp Gly Arg
```

-continued

```
                        500                 505                 510
atg act gta gag gta tat ggt tat aat ata tcc aca cta gga aat tat       1584
Met Thr Val Glu Val Tyr Gly Tyr Asn Ile Ser Thr Leu Gly Asn Tyr
                    515                 520                 525 att acg gag tga                                                       1596
Ile Thr Glu
        530

<210> SEQ ID NO 12
<211> LENGTH: 741
<212> TYPE: DNA
<213> ORGANISM: Ferroplasma acidiphilum
<220> FEATURE:
<221> NAME/KEY: CDS
<222> LOCATION: (1)..(741)
<223> OTHER INFORMATION: glu FA, in Figure 11 designated sequence 7a

<400> SEQUENCE: 12 atg gaa att cag gat atc gat tta act att gtt tta gca act ctt aac        48
Met Glu Ile Gln Asp Ile Asp Leu Thr Ile Val Leu Ala Thr Leu Asn
1               5                  10                  15 gaa ata gat aat ctt cca cgg ctc tgt tct gat atc gat tca ata tta        96
Glu Ile Asp Asn Leu Pro Arg Leu Cys Ser Asp Ile Asp Ser Ile Leu
                20                  25                  30 aaa aat acg aaa ata aag tat cag tta tta ttt gtc gat gat aac agt       144
Lys Asn Thr Lys Ile Lys Tyr Gln Leu Leu Phe Val Asp Asp Asn Ser
            35                  40                  45 agc gat gga acc aga gag ttt att ata gag tat tgc aat aaa aat aaa       192
Ser Asp Gly Thr Arg Glu Phe Ile Ile Glu Tyr Cys Asn Lys Asn Lys
        50                  55                  60 tta tca aaa tat att ttt aat gaa tac aag aaa tca acc ctt ata gcc       240
Leu Ser Lys Tyr Ile Phe Asn Glu Tyr Lys Lys Ser Thr Leu Ile Ala
65                  70                  75                  80 aga tac cag gga ata aac aat gca gat ggg aaa tat att ata ctt atg       288
Arg Tyr Gln Gly Ile Asn Asn Ala Asp Gly Lys Tyr Ile Ile Leu Met
                85                  90                  95 gat tca gat ttg caa cat ccc cca aaa tat ctc tta aat ata tat aac       336
Asp Ser Asp Leu Gln His Pro Pro Lys Tyr Leu Leu Asn Ile Tyr Asn
                100                 105                 110 agt tta ttg aaa cat aat gat atc gta att gcc agc aga tac gtt aaa       384
Ser Leu Leu Lys His Asn Asp Ile Val Ile Ala Ser Arg Tyr Val Lys
            115                 120                 125 ggt ggc agt acc gga aat cgc aaa cct ata cgt ggc att ata tca cgt       432
Gly Gly Ser Thr Gly Asn Arg Lys Pro Ile Arg Gly Ile Ile Ser Arg
        130                 135                 140 ggg gca tct ttg atg gca caa cta cta ttg aaa agc agc agg cag ata       480
Gly Ala Ser Leu Met Ala Gln Leu Leu Leu Lys Ser Ser Arg Gln Ile
145                 150                 155                 160 aag gac ccc ata tcg tgt tat att ggc ttt aga aaa ggg ctg aaa ttg       528
Lys Asp Pro Ile Ser Cys Tyr Ile Gly Phe Arg Lys Gly Leu Lys Leu
                165                 170                 175 gat ata gac gaa ggc tgg aga ggc tat gag ata ggt att ttc tta agg       576
Asp Ile Asp Glu Gly Trp Arg Gly Tyr Glu Ile Gly Ile Phe Leu Arg
                180                 185                 190 gct agc aat aat aat gtt aag gta aag gaa ata cct tat cga ttt gcg       624
Ala Ser Asn Asn Asn Val Lys Val Lys Glu Ile Pro Tyr Arg Phe Ala
            195                 200                 205 gaa agg gaa aat gga aaa tca aaa gta acg tcc agt gta aaa ttt tta       672
Glu Arg Glu Asn Gly Lys Ser Lys Val Thr Ser Ser Val Lys Phe Leu
        210                 215                 220 aga gtt tat ata ata gaa tta tta ttg gca aaa aga gtt gag ata aga       720
Arg Val Tyr Ile Ile Glu Leu Leu Leu Ala Lys Arg Val Glu Ile Arg
```

```
                225                 230                 235                 240
        aat tat aaa cca att ttg tga                                              741
        Asn Tyr Lys Pro Ile Leu
                    245

<210> SEQ ID NO 13
<211> LENGTH: 1086
<212> TYPE: DNA
<213> ORGANISM: Ferroplasma acidiphilum
<220> FEATURE:
<221> NAME/KEY: CDS
<222> LOCATION: (1)..(1086)
<223> OTHER INFORMATION: glu FA2, in Figure 11 designated sequence 9a

<400> SEQUENCE: 13 atg aaa ata act tac cac aag cta aaa atg cca ctg ata agc cca ttc        48
Met Lys Ile Thr Tyr His Lys Leu Lys Met Pro Leu Ile Ser Pro Phe
1               5                   10                  15 aca acc agc ttc gga aca gat gta aac aag gat gtt tat gtt ttc aag        96
Thr Thr Ser Phe Gly Thr Asp Val Asn Lys Asp Val Tyr Val Phe Lys
                20                  25                  30 ctt gaa cat aat gga ata act gct tat tct gaa agt gtt acc gac gaa       144
Leu Glu His Asn Gly Ile Thr Ala Tyr Ser Glu Ser Val Thr Asp Glu
            35                  40                  45 aat cct ttt tat ggc tca gaa gat aat tat aca gta ttc cat att gta       192
Asn Pro Phe Tyr Gly Ser Glu Asp Asn Tyr Thr Val Phe His Ile Val
        50                  55                  60 aaa cag tat ctt gca cca gta gta aaa ggc ctt cca gag ccg gat gaa       240
Lys Gln Tyr Leu Ala Pro Val Val Lys Gly Leu Pro Glu Pro Asp Glu
65                  70                  75                  80 ttc aat gaa cag gta aaa ttt ata aaa ggc aat aat atg gca aaa gct       288
Phe Asn Glu Gln Val Lys Phe Ile Lys Gly Asn Asn Met Ala Lys Ala
                85                  90                  95 tcc atg gaa atg ctt ctc tat gat tat tat gca aaa gca aat aaa aaa       336
Ser Met Glu Met Leu Leu Tyr Asp Tyr Tyr Ala Lys Ala Asn Lys Lys
                100                 105                 110 tcc ctg gta gat tac ata ggg cac agc agg gga tat gca aac gtt gga       384
Ser Leu Val Asp Tyr Ile Gly His Ser Arg Gly Tyr Ala Asn Val Gly
            115                 120                 125 ata tca ctt gga atg gat gat ata aac gtt aca tta aag aag ata cag       432
Ile Ser Leu Gly Met Asp Asp Ile Asn Val Thr Leu Lys Lys Ile Gln
        130                 135                 140 gaa gcc ctt gac cgt gga tat aaa aga att aaa gtc aaa ata atg aag       480
Glu Ala Leu Asp Arg Gly Tyr Lys Arg Ile Lys Val Lys Ile Met Lys
145                 150                 155                 160 gga aag gaa ata ggt ata cta agt gct gta agg gac aat ttt ccg gat       528
Gly Lys Glu Ile Gly Ile Leu Ser Ala Val Arg Asp Asn Phe Pro Asp
                165                 170                 175 ata gtt tta agt gca gac gcc aac agc gat tat acc gag aag gat ttt       576
Ile Val Leu Ser Ala Asp Ala Asn Ser Asp Tyr Thr Glu Lys Asp Phe
            180                 185                 190 gat ttg att aaa aaa ata gac aga tac aat ctt gta tat ctg gag cag       624
Asp Leu Ile Lys Lys Ile Asp Arg Tyr Asn Leu Val Tyr Leu Glu Gln
        195                 200                 205 ccc ctg tac cat gat gat ata ata tac cat tca agg ctt gca aag gga       672
Pro Leu Tyr His Asp Asp Ile Ile Tyr His Ser Arg Leu Ala Lys Gly
    210                 215                 220 tta tcc acg cca tta tgc ctg gat gaa tct att act tca ccg gag aag       720
Leu Ser Thr Pro Leu Cys Leu Asp Glu Ser Ile Thr Ser Pro Glu Lys
225                 230                 235                 240 gca cag aaa gca ttt gaa atg ggt gcg tgt aag gtt ata aac ata aaa       768
Ala Gln Lys Ala Phe Glu Met Gly Ala Cys Lys Val Ile Asn Ile Lys
```

-continued

```
                       245                     250                     255
gag gga agg cta ggc gga atc gga aat tcc tta aaa gtt atg gga ata            816
Glu Gly Arg Leu Gly Gly Ile Gly Asn Ser Leu Lys Val Met Gly Ile
            260                     265                     270 gtg aag gaa ttc aag ggc cat gta tgg att gga gga atg tta gaa act            864
Val Lys Glu Phe Lys Gly His Val Trp Ile Gly Gly Met Leu Glu Thr
            275                     280                     285 gga atc gga agg tcc ttt aat gtt tcc atg gca tct ctt tct gat att            912
Gly Ile Gly Arg Ser Phe Asn Val Ser Met Ala Ser Leu Ser Asp Ile
            290                     295                     300 aat tat cct gga gac aca tcg ccc aat gac aaa tac ttt aaa aat gac            960
Asn Tyr Pro Gly Asp Thr Ser Pro Asn Asp Lys Tyr Phe Lys Asn Asp
305                     310                     315                     320 ata gtt aag aat cca ttc aca atg gaa aat ggc aca att aag cct aat           1008
Ile Val Lys Asn Pro Phe Thr Met Glu Asn Gly Thr Ile Lys Pro Asn
            325                     330                     335 aag ggt aca ggc atc ggt gtt gaa atc agt gaa gag tat cta aaa aaa           1056
Lys Gly Thr Gly Ile Gly Val Glu Ile Ser Glu Glu Tyr Leu Lys Lys
            340                     345                     350 tat acc gtt gaa gag ggg ata ata gca tga                                   1086
Tyr Thr Val Glu Glu Gly Ile Ile Ala
            355                     360
```

ACIDOPHILIC ENZYMES

The present invention relates to enzymes having catalytic activity at a pH below 5.0. The present invention provides hydrolyzing enzymes obtainable from archaeobacteria, in detail to hydrolytic enzymes obtainable from the archaeobacterium *Ferroplasma acidiphilum*, requiring $Fe^{2+}$ for catalytic activity.

At present, it is common knowledge that extremophilic microorganisms, e.g. archaeobacteria adapt to the extremophilic habitat by strictly controlling their intracellular pH. This finding is based on analytical results obtained from acidophilic archaeobacteria, showing that the intracellular, i.e. the physiological pH value which intracellular enzymes are adapted to is in the range of 5.6.

STATE OF THE ART

Xiao et al. (PNAS, 100, No. 9, 5205-5210) have shown that acidic pH values interfere with topoisomerase II activity, both in vitro and in mammalian cells. Accordingly, acidic pH is regarded as a cause for topoisomerase II induced DNA damage, i.e. mutation, and a possible cause of cancer. Experiments demonstrate that a pH below 7.0, having an optimum at about 5, causes the formation of a stable complex between topoisomerase II and DNA to be religated in an in vitro assay. The stabilization of this enzymatic complex interrupts the normal function of topoisomerase II, leading to DNA damage.

GENERAL DESCRIPTION OF THE INVENTION

In general, the present invention provides enzymes which are active and stable at acidic pH values, especially at pH values from 1 to 4, especially in the range of pH 2 to 3, obtainable from *Ferroplasma acidiphilum*, especially to an esterase, glycosidases and a DNA ligase. In addition to stability and activity at low pH values, the enzymes according to the present invention are all dependent on $Fe^{2+}$ for their catalytic activity, which can be removed by complexing agents such as EDTA in a reversible manner. Further, $Fe^{2+}$ has been shown to act as a cofactor in these enzymes, which is in accordance with inactivation of the enzyme by oxidation of $Fe^{2+}$ to $Fe^{3+}$ and the impact of different cations that might replace $Fe^{2+}$ and substances possibly interfering with $Fe^{2+}$.

Using high-resolution two-dimensional gel electrophoresis on separate membrane and cytoplasmic protein fractions of *Ferroplasma acidiphilum*, grown at 37° C. in medium 9K at pH 1.7, followed by Q-TOF mass spectrometry on single, well resolved spots, it could be demonstrated that Seta and αGluFA are membrane associated, whereas LigFA, GlyFA1 and GlyFA2 are intracellular cytoplasmic enzymes.

Results of different salts and interfering substances are comprised in the following Table I, showing alterations in activity of acidic esterase (EstFA), acidic glucosidase (αGluFA) and acidic ligase (LigFA) in response to different additives.

The enzymes used for the tests were heterologously expressed in *E. coli* using genomic coding sequences obtained from *Ferroplasma acidiphilum*.

TABLE I

Effect of cations and inhibitors on recombinant EstFA, LigFA and αGluFA

| | | Activity (%) | | |
|---|---|---|---|---|
| Additive | mM | EstFA | αGluFα | LigFA |
| None | | 100 | 100 | 100 |
| $NH_4^+$ | 10 | 85.2 | 103.8 | 107.2 |
| | 125 | 97.1 | 58.8 | 108.2 |
| $Li^+$ | 10 | 100.2 | 107.2 | 101.6 |
| | 125 | 48.0 | 69.4 | 107.9 |
| $Na^+$ | 10 | 102.8 | 86.3 | 71.1 |
| | 125 | 91.2 | 74.0 | 100 |
| $K^+$ | 10 | 108.5 | 86.0 | 129.9 |
| | 125 | 115.7 | 76.3 | 93.8 |
| $Ca^{2+}$ | 10 | 116.3 | 91.2 | 126.2 |
| | 125 | 100.8 | 74.1 | 81.6 |
| $Mg^{2+}$ | 10 | 106.1 | 92.2 | 157.0 |
| | 125 | 116.8 | 64.7 | 126.8 |
| $Zn^{2+}$ | 10 | 57.8 | 1.1 | 5.3 |
| | 125 | 4.6 | 16.2 | 10.2 |
| $Sr^{2+}$ | 10 | 102.1 | 98.0 | 90.7 |
| | 125 | 106.5 | 71.3 | 20.2 |
| $Co^{2+}$ | 10 | 55.2 | 72.0 | 102.5 |
| | 125 | 68.3 | 82.8 | 88.7 |
| EDTA | 10 | 16.0 | 10.6 | 17.2 |
| | 125 | 9.5 | 9.4 | 7.0 |
| Triton X-100 | 1% | 74.6 | 95.7 | 62.3 |
| | 3% | 43.5 | 47.4 | 9.0 |
| SDS | 10 | 75.2 | 2.4 | 32.6 |
| | 50 | 47.3 | 0.5 | 27.5 |
| mercaptoethanol | 1 | 55 | n.d. | n.d. |
| PMST | 1 | 52 | n.d. | n.d. |

Figure 2:
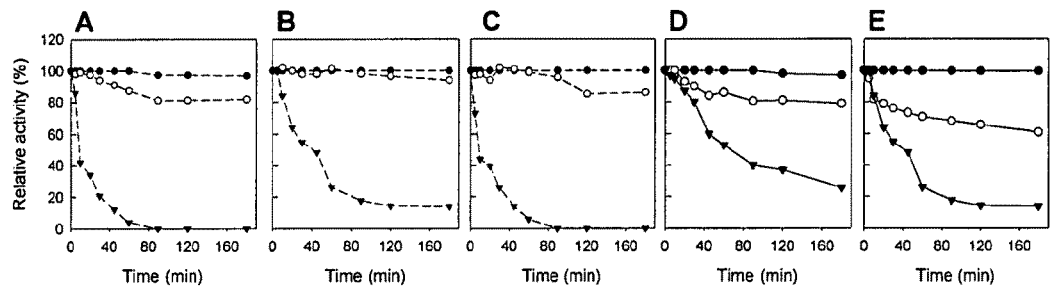
Figure 3:
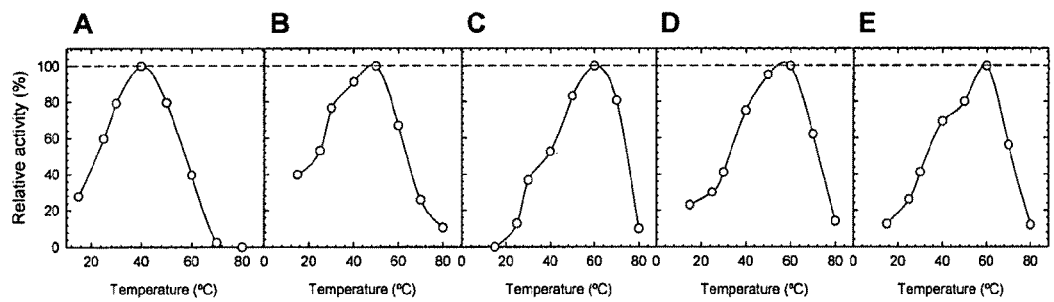
Figure 4:
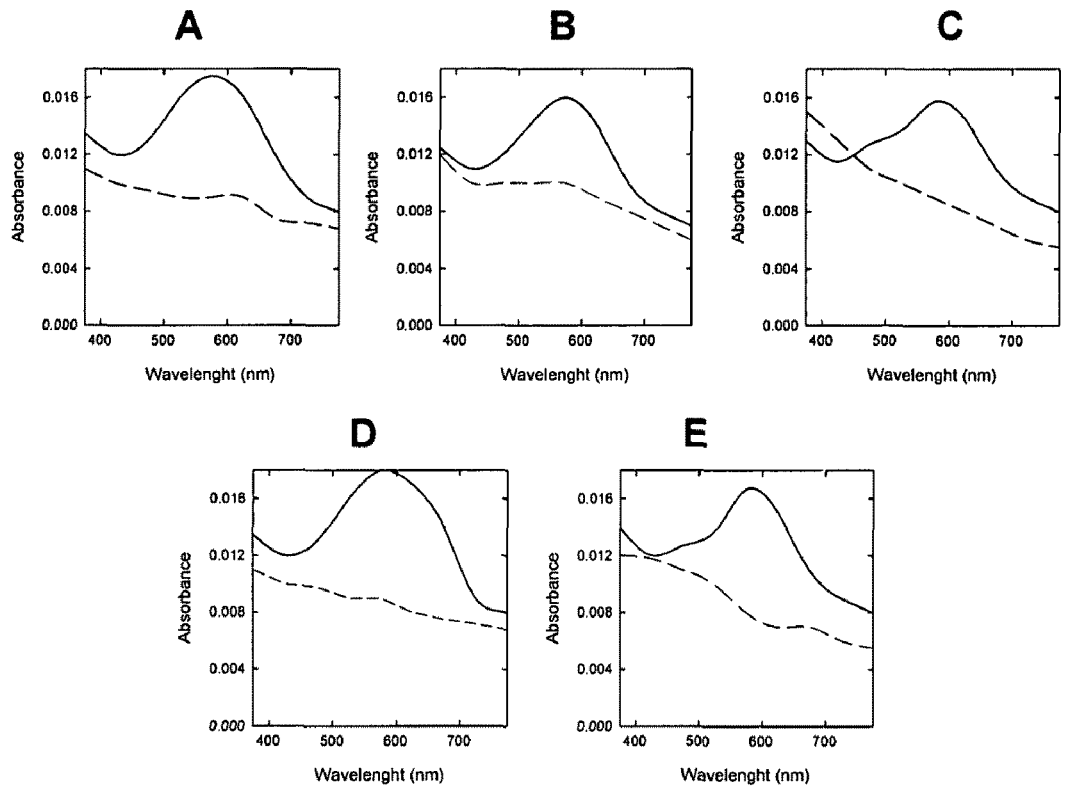
Figure 5:
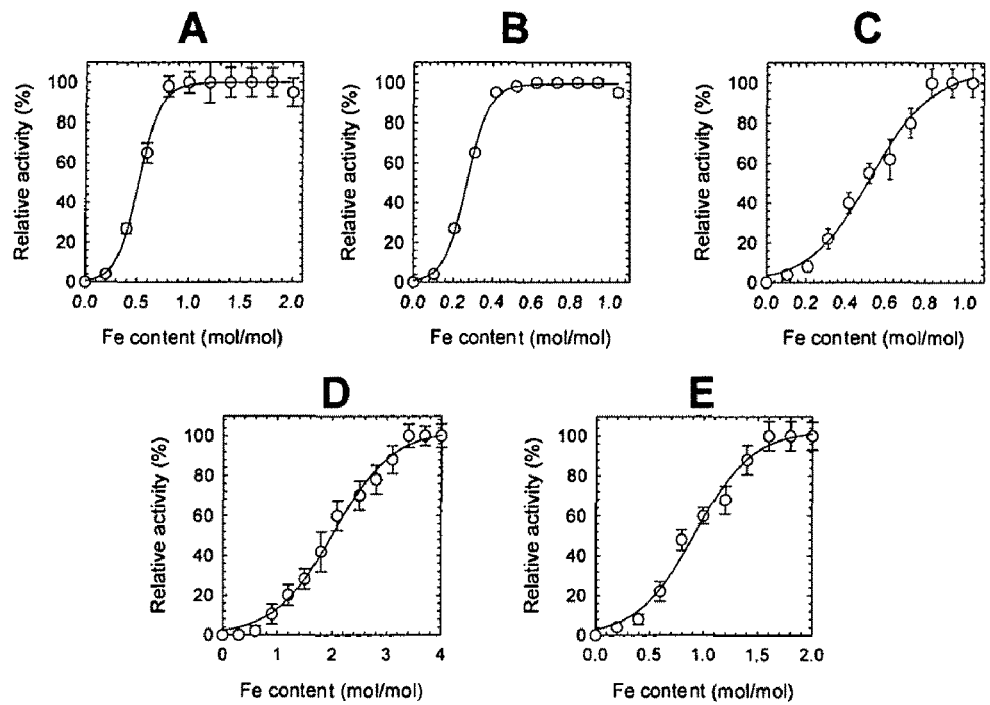
Figure 6:
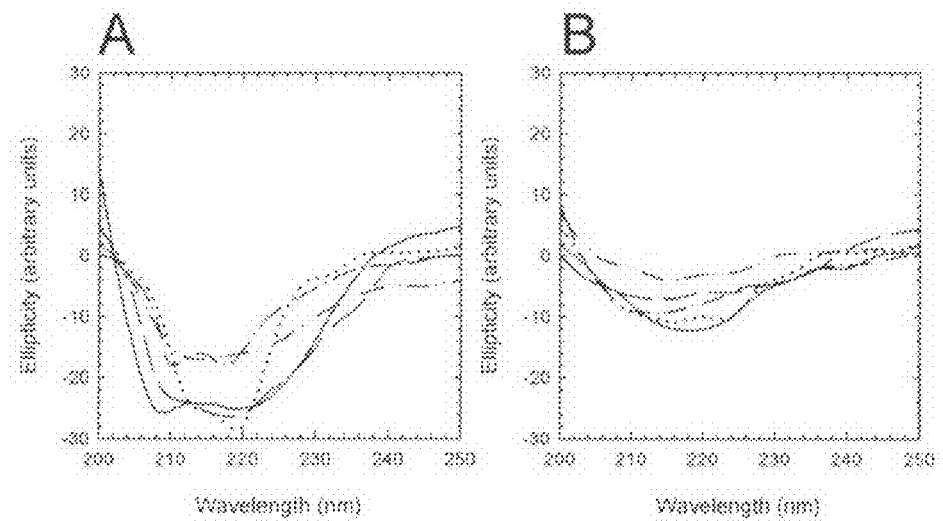

Characteristic properties for the enzymes according to the invention are now described in greater detail with reference to the figures, wherein FIG. 1 shows the activities of acidic ligase LigFA (A), acidic esterase EstFA (B), and acidic glycosidases αGluFA (C), GlyFA1 (D), GlyFA2 (E) from *Ferroplasma acidiphilum* in 100 mM buffer: sodium citrate (○), sodium acetate (□) and MES (morpholine ethanesulfonic acid (Δ), respectively, FIG. 2 shows the temperature stability of LigFA (A), EstFA (B), and αGluFA (C), GlyFA1 (D), GlyFA2 (E) from *Ferroplasma acidiphilum*. Buffers for esterase and glycosidase were 100 mM citrate buffer, pH 2.0 for GlyFA1 and EstFA, 3.0 for LigFA and 4.0 for αGluFA and GlyFA2 at 40 (●), 50° C. (○) and 70° C. (▼);

FIG. 3 shows the temperature dependence of the enzymatic activities for LigFA (A), EstFA (B), and αGluFA (C), GlyFA1 (D), GlyFA2 (E), reactions were carried out in 100 mM citrate buffer, pH 2.0 for GlyFA1 and EstFA, 3.0 for LigFA and 4.0 for αGluFA and GlyFA2;

FIG. 4 shows UV-VIS absorption spectra of purified LigFA (A), EstFA (B), and αGluFA (C), GlyFA1 (D), GlyFA2 (E) before and after dialysis of the enzyme against buffer containing EDTA, FIG. 5 shows the dependence of the enzymatic activity on $Fe^{2+}$ of LigFA (A), EstFA (B), and αGluFA (C), GlyFA1 (D), GlyFA2 (E), and FIG. 6 shows circular dichroism spectra for enzymes containing $Fe^{2+}$ (A) and without $Fe^{2+}$ (B) for LigFA (..........), EstFA (---), αGluFA (_____), GlyFA1 (-.-.) and GlyFA2 (-..-..-).

The acidic enzymes according to the invention were expressed in *E. coli* using the genomiccoding sequence for the respective enzyme from *Ferroplasma acidiphilum*, which are described in detail below. For enzymatic conversions, reaction conditions were in 100 mM sodium acetate buffer, 100 mM citrate buffer, 100 mM HEPES buffer for 2 minutes at 30° C., using p-nitrophenol propionate as the substrate for esterase, starch in the case of glycosidases, and HindIII digested λ DNA for ligase.

Results are shown in FIG. 1, demonstrating that the enzymes are active at pH values as low as 1 to 4, with the possibility of using very low pH values of approximately pH 2 to 3 or 4 for LigFA, pH 1 to 3 for EstFA, and pH 1.5 to 6 for αGluFA as well as pH 1.5 to 4 for GluFA1 and pH 3 to 6 for GluFA2, respectively. In FIG. 1, 100% activity was determined as $k_{cat}/K_M$ values of 300 s$^{-1}$ mM$^{-1}$ for LigFA, 64.2 s$^{-1}$ mM$^{-1}$ for EstFA, 197 s$^{-1}$ mM$^{-1}$ for αGluFA, 95 s$^{-1}$ mM$^{-1}$ for GlyFA1 and 142 s$^{-1}$ mM$^{-1}$ for GlyFA2.

The data for enzymatic stability of acidic enzymes according to the invention at elevated temperatures could demonstrate good stability of the each enzyme at the acidic range of its respective optimum pH value, especially a good stability for LigFA at pH 3.0 for 40 and 50° C., for EstFA and αGluFA at pH 2.0 for 40 and 50° C. as well as for GlyFA1 and GlyFA2 at pH 4.0 at 40° C., less at 50° C. and decreasingly at 70° C. The activity was assayed using p-nitrophenol propionate as a substrate for esterase, starch for αGluFA and GlyFA1, GlyFA2, and HindIII digested λ DNA for LigFA. Results are shown in FIG. 2.

The acidic enzymes according to the invention in vitro show similar elevated reaction temperatures. The temperature dependence of the activity is shown in FIG. 3. Substrates were as described for FIG. 2 above. The data show that optimum temperatures for LigFA is about 40° C., for EstFA about 44° C., for αGluFA about 60° C., for GlyFA1 and GlyFA2 58 and 60° C., respectively, at the pH value indicated.

The UV-VIS absorption spectra of purified acidic enzymes are shown in FIG. 4, wherein the uninterrupted lines refer to Fe$^{2+}$ containing enzymes and the interrupted lines refer to enzymes after dialysis against EDTA containing buffer. The λ-max values found at ca. 572 nm correlate with the Fe$^{2+}$ content, i.e. disappear after incubation with EDTA or DTT for 24 h. ICP-MS analysis confirmed the presence of 0.82±0.10 mol Fe in EstFA, 0.34±0.08 mol Fe in αGluFA, in G and 0.63±0.09 mol Fe in LigFA.

In FIG. 5, relative activities of acidic enzymes with varying content of Fe$^{2+}$ are shown. For analysis, purified enzymes were incubated in 1 mM EDTA. At time intervals indicated, two aliquots were removed, one was used for hydrolysis of respective substrates, the other for ICP-MS analysis of Fe. For relative activities, activities before incubation with EDTA were used as 100% values.

It can be seen that activity is dependent on Fe$^{2+}$, increasing sharply in the range of 0.1 mole/mole to 0.3 mole/mole for EstFA, αGluFA, GlyFA1 and GlyFA2, respectively, and less steeply for ligFA over the range up to 0.9 mole/mole Fe$^{2+}$, in each case reaching a saturation concentration.

When further investigating the dependence of the acidic enzymes according to the invention on Fe$^{2+}$, relative activity for EstFA, αGluFA and LigFA were investigated for their natural Fe$^{2+}$ content, e.g. wild-type, which was set to 100%, in comparison to the activity after dialysis against a 1 mM EDTA containing buffer. Relative contents of metal (Fe$^{2+}$) and activities are given in the following Table II.

TABLE II

Comparison of metal content and relative activities of acidic enzymes from Ferroplasma acidiphilum

| variant | wild type | | +EDTA | |
|---|---|---|---|---|
| | metal: protein[a] | activity[b] | metal: protein[a] | activity[b] |
| LigFA | 2.03 ± 0.09 | 100 | 0.06 | 0.15 |
| EstFA | 1.03 ± 0.10 | 100 | 0.09 | 0.30 |
| αGluFA | 1.04 ± 0.08 | 100 | 0.05 | 5.40 |
| GlyFA1 | 4.08 ± 0.10 | 100 | 3.03 | 5.20 |
| GlyFA2 | 2.02 ± 0.08 | 100 | 0.04 | 3.00 |

[a] Metal content is shown as moles Fe$^{2+}$ per mole of enzyme ± standard deviation, calculated from three independent analyses.
[b] Enzyme activity was measured in 100 mM sodium citrate buffer, containing 10 mM FeCl$_2$ at the following pH and temperature (EstFA: pH 2.0, 45° C.; αGluFA pH 3.0, 57° C.; LigFA, pH 2.8, 40° C.).

An overview of catalytic and molecular properties of acidic enzymes that were heterologously expressed in E. coli is given in the following Table III:

TABLE III

Properties of recombinant acidic enzymes

| parameter | LigFA | EstFA | αGluFA | GlyFA1 | GlyFA2 |
|---|---|---|---|---|---|
| [a] Optimum temperature [° C.] | 40 | 50 | 60 | 60 | 60 |
| [a] Optimum pH | 1.5-3.0 | 2.0-3.5 | 2.5-3.0 | 2.0 | 3.5-4.0 |
| [a] half life [min] | 80 (pH 2.5, 40° C.) | 48 (pH 2.0, 50° C.) | 34 (pH 2.5, 60° C.) | 20 (pH 2.0, 60° C.) | 12 (pH 4.0, 60° C.) |
| [a] half life [min] | 3.7 (pH 6.0, 40° C.) | 1.2 (pH 6.0, 50° C.) | 9.3 (pH 6.0, 60° C.) | 1.6 (pH 6.0, 60° C.) | 3.3 (pH 6.0, 60° C.) |
| apparent Mr, native enzyme [10$^3$] | 68 | 35 | 57 | 56 | 80 |
| [b] apparent Mr, subunit [10$^3$] | 67 (67.84) | 36 (34.73) | 57 (57.3) | 28 (28.32) | 42 (40.50) |
| pI | 5.13 | 5.91 | 6.42 | 9.53 | 6.42 |
| Metal ion required | Fe$^{2+}$ | Fe$^{2+}$ | Fe$^{2+}$ | Fe$^{2+}$ | Fe$^{2+}$ |

[a] measured at optimum pH and temperature, respectively
[b] theoretical molecular masses given in brackets I. Acidic Ligase In a first aspect, the present invention relates to a DNA ligase obtainable from Ferroplasma acidiphilum having its pH optimum below pH 4. This ligase, subsequently termed LigFA is strongly dependent on Fe$^{2+}$. It was found that for optimum in vitro activity, a concentration of Fe$^{2+}$ from 2 to 18 mM, with an optimum at 10 mM is necessary. In the presence of 10 mM Fe$^{2+}$, the optimum pH is 1.5 to 3.0 and the enzyme is stable up to pH 5, where the half life of LigFA is less than 20 minutes. The temperature for optimum activity was determined to be approximately 40° C.

LigFA obtained from Ferroplasma acidiphilum was found to contain 595 amino acids, having a theoretical molecular weight of 67,841 Da and a theoretical isoelectric point of 5.13. Size exclusion chromatography of the enzyme purified after heterologous expression in E.coli suggests a native molecular mass of 135600 Da, consistent with LigFA being a dimer. The nucleic acid sequence is given as Seq. ID No. 1, the amino acid sequence as Seq. ID No. 3.

The enzymatic activity is dependent on the presence of ATP. In activity measurements, a $k_{cat}/K_M$ value of 300 s$^{-1}$ mM$^{-1}$ was defined as 100% activity.

Sequence analysis according to Nakatani et al. (J. Bacteriol. 182, 6424-6433 (2000)) revealed a nucleotide binding site K$_{263}$QDG, a ribose binding residue (IIIDGE$_{313}$SV), a purine ring stacking residue VMFIF$_{354}$DILELNG), and a phosphate binding residue WIK$_{437}$FKRDYQKE.

II. Esterase

In a second aspect, the present invention relates to an acidophilic, Fe$^{2+}$ dependent esterase obtainable from *Ferroplasma acidiphilum*.

Acidic esterase, subsequently termed EstFA was found to be active at acidic pH values, having an optimum at pH 2.0 to 3.5 using for example 100 mM sodium citrate buffer containing 100 µM FeCl2, using p-nitrophenol propionate (pNPP) as a substrate.

For ester hydrolysis or synthesis, purified acidic esterase, for example obtained by heterologous expression can be used or, alternatively, wet and/or lyophilized cell and/or membrane extracts. In activity measurements, a k$_{cat}$/K$_M$ value of 64.2 s$^{-1}$ mM$^{-1}$ was defined as 100% activity.

The genomic gene for EstFA encodes a 308 amino acid esterase, having a theoretical molecular weight of 34734 Da, and an isoelectric point (pI) of 5.91. The DNA sequence is given as Seq. ID No. 4 and the amino acid sequence translated from the nucleic acid sequence as Seq ID No. 6.

According to comparative studies of the amino acid sequence, EstFA belongs to the ester hydrolase family IV of the Arpigny and Jaeger classification (Biochem. J. 343, 177-183 (1999)), containing the conserved motive (/GDSAG/, /DPL/, /HGS/), probably having a catalytic triad formed by Serine 156, D251 and H281.

For production of EstFA enzyme by heterologous expression as encoded by *Ferroplasma acidiphilum*, e.g. in *E. coli*, a strict requirement for Fe$^{2+}$ ions having an optimum at a concentration of 4.5 mM was determined. Size exclusion analysis of the purified enzyme suggests a native molecular mass of 103500 Da, consistent with EstFA being a trimer. The optimum pH value for EstFA was established using 100 mM sodium acetate, citrate and HEPES, the ionic strength of which remains constant over the pH range tested of 1 to 5.5. The optimum pH was found to be 2.0 to 3.5, whereas EstFA was rapidly inactivated at pH values above 5.0. Purified EstFA was stable in 20 mM citrate buffer, pH 1.5 for several days at room temperature. The optimum temperature for catalysis was determined to lie between 40 and 50° C.

It was found that divalent cations of nickel, cobalt, manganese, calcium or magnesium could not substitute Fe$^{2+}$ when provided at a concentration of 1 to 0 µM as chloride salts. In contrast, EstFA was inhibited by about 5 to 14% when the aforementioned divalent atoms were provided in addition to 1 to 0 µM FeCl$_2$. Complexing of Fe$^{2+}$ by added EDTA inhibited the activity of EstFA in a reversible manner. When analysing the substrate specificities of EstFA, it was found that for the compounds tested, hydrolysis was better for primary or secondary alcohols (menthyl acetate), showing some enantioselectivity. The activity of EstFA towards p-nitrophenol esters of fatty acids with varying chain lengths (C2 to C12) showed a preference for hydrolysis of short-chain and medium-chain length fatty acids (C2-C8), whereas longer chain fatty acids were poor substrates. Additionally, triolein was not hydrolysed, suggesting that the enzyme is an esterase rather than a lipase.

When characterizing the activity of EstFA toward esters, optionally containing a stereocentre in α- or β-position to the carbonyl group, hydrolytic rates were determined for primary and secondary alcohols (menthyl acetate) and chiral carboxylic acids (methyl-3-hydroxy butyrate and methyl-3-hydroxy-2-menthyl propionate) or a lactone (di-hydro-5-hydroxymethyl-2 (3H) furanol). Hydrolysis was found to be enantioselective, at least to some degree specific for one enantiomer.

III. Acidic Glycosidases

In a third aspect, the present invention relates to acidic glycosidases obtainable from *Ferroplasma acidiphilum*.

From the glycosidases identified, αGluFA was determined to encode a 531 amino acid protein, giving a theoretical molecular weight of 57300 Da, an isoelectric point of 6.42, estimated to be 57000 of the basis of relative mobility on an SDS- and native polyacrylamide gel in comparison to the size marker protein. The glycosidases are dependent on ferrous ions, Fe$^{2+}$, with an optimum concentration of 4.5 to 14.2 mM. The optimum pH of the purified glycosidase was 2.0. αGluFA was stable in a range of pH 1.5 to 3.9, in which range the enzyme retained more than 80% of its original activity after an incubation at 20° C. over 24 hours. Highest activity was obtained at 60° C. for a reaction time of 30 minutes and the enzyme was stable up to 60° C. for 60 minutes, at 65° C., approximately 50% of the enzymatic activity were retained (FIG. 3).

Furthermore, acidic glycosidases termed GlyFA1 and GlyFA2 were cloned from *Ferroplasma acidiphilum* in a similar way as αGluFA.

In activity measurements, k$_{cat}$/K$_M$ values of 197 s$^{-1}$ mM$^{-1}$ for αGluFA, 95 s$^{-1}$ mM$^{-1}$ for GlyFA1 and 142 s$^{-1}$ mM$^{-1}$ for GlyFA2 were defined as 100% activity.

The sequences of glycosidases are given for αGluFA as nucleic acid sequence Seq ID No. 7 and amino acid sequence Seq ID No. 11, for GluFA1, nucleic acid sequence as Seq ID No. 12 and amino acid sequence Seq ID No. 16, and for GluFA2 as nucleic acid sequence Seq ID No. 17 and amino acid sequence Seq ID No. 22.

Figure 7:
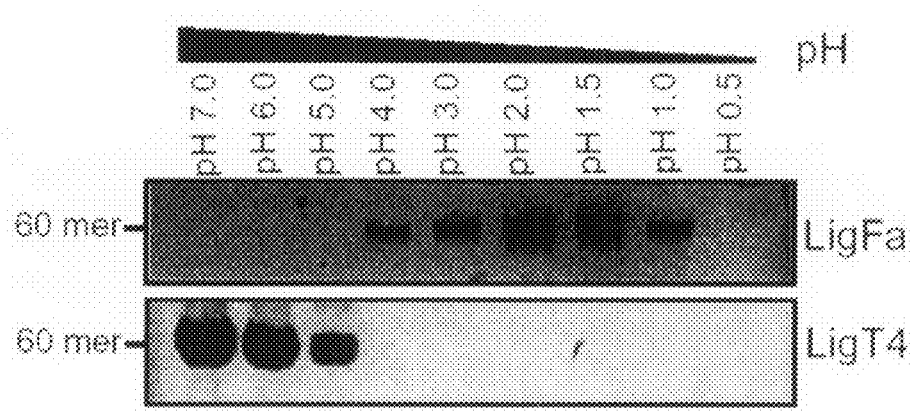
Figure 8:
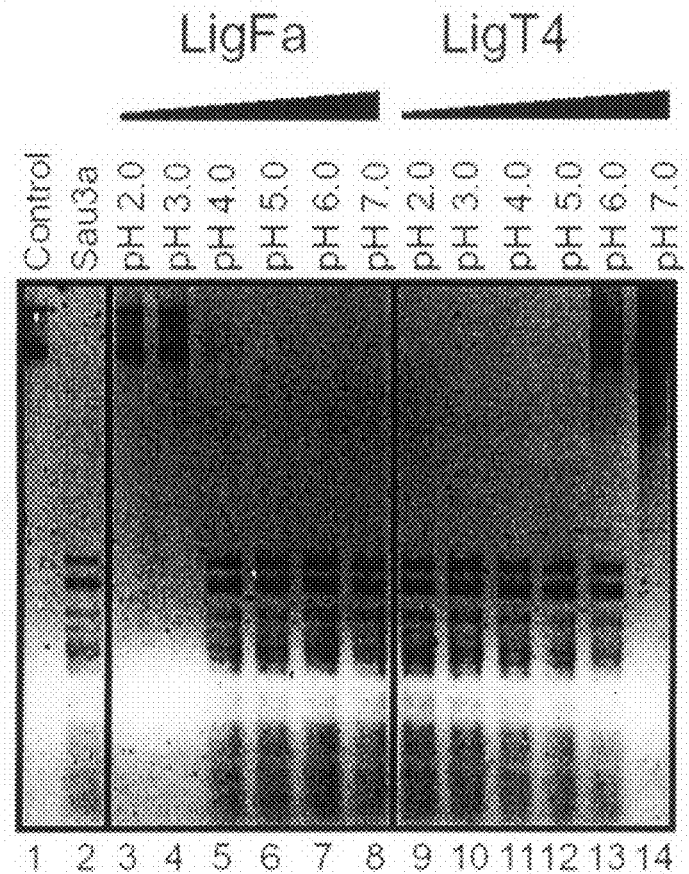
Figure 9:
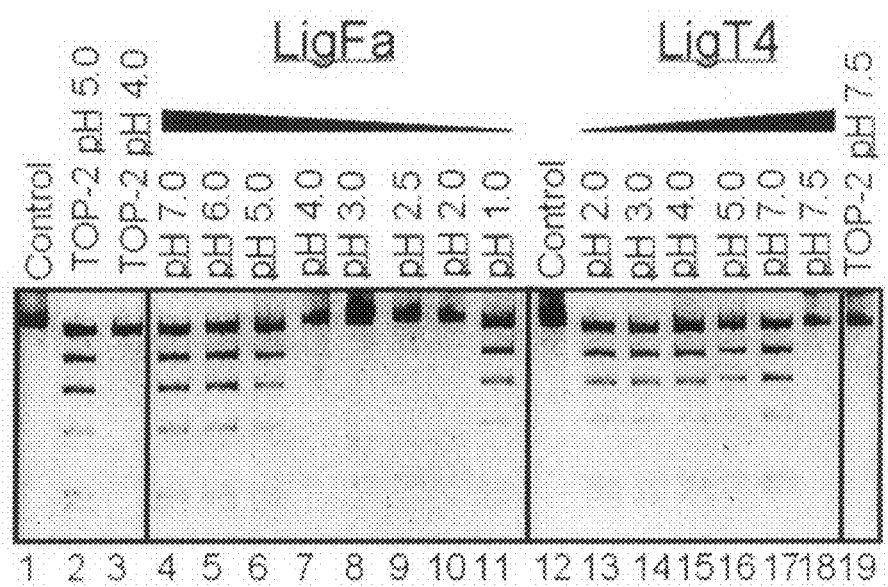
Figure 10:
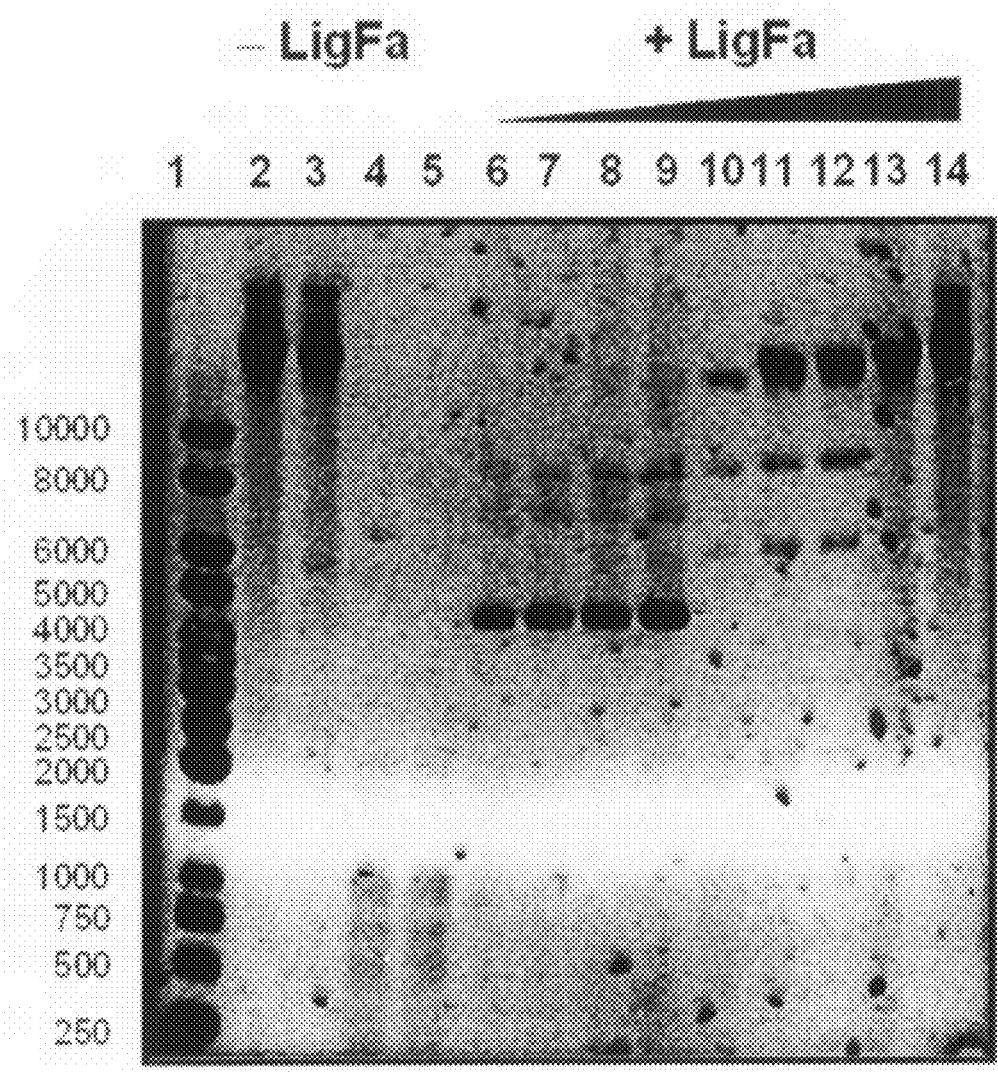

The present invention will now be described in greater detail by way of examples with reference to the figures, wherein FIG. 7 shows a partial denaturing polyacrylamide gel of ligation products obtained from the ligation of oligonucleotides at different pH values, FIG. 8 shows a non-denaturing agarose gel of ligation products of restricted Sau3A digested bacteriophage λ DNA of LigFA and T4 ligase (comparison), FIG. 9 shows a non-denaturing agarose gel of ligation products obtained from restricted λ DNA ligated with LigFA and T4 ligase (LigT4) for comparison, at varying pH values, FIG. 10 shows a non-denaturing agarose gel of a one-tube restriction-ligation reaction on Sau3A digested bacteriophage λ DNA using LigFA, and FIG. 11 contains sequence data.

EXAMPLE 1

Cloning of Acidophilic Ligase from *Ferroplasma acidiphilum* (ligFA)

For isolation of the genomic copy of the ligFA gene, total DNA isolated from *Ferroplasma acidiphilum* (strain DSMZ 12658) was subjected to PCR using primers having Seq ID No. 1 and Seq ID No 2, wherein additional endonuclease sites for NdeI and BamHI are shown in bold. For PCR, an initial denaturation at 95° C. for 120 seconds, followed by 30 cycles of 95° C., 45 seconds, 50° C., 60 seconds, 72° C., 120 seconds was used, followed by a final extension at 72° C. for 500 seconds. The amplification product of approximately 1800 base pairs was purified by agarose gel electrophoresis, extracted from the gel (QiaEx II gel extraction kit, Qiagen, Hilden, Germany), and ligated into plasmid PCR 2.1 using the TOPO TA cloning kit (Invitrogen, California, USA). For plasmid amplification, the ligation products were electroporated into *E. coli* DH5α electrocompetent cells (Invitrogen) and positive clones were selected on kanamycin containing LB agar plates. For sequencing amplification fragments, M13 and rM13 oligonucleotide primers were used and fragments containing sequences encoding LigFA were excised from plasmids using endonucleases NdeI and BamHI.

EXAMPLE 2

Expression of Acidophilic Ligase LigFA in *E. coli*

DNA fragments encoding LigFA were excised from plasmids according to Example 1 and isolated by gel electrophoresis, then ligated into an expression vector (e.g. PET-3a by Novagen), pre-digested with the same endonucleases and dephosphorylated. After transformation of an *E. coli* expression host (*E. coli* BL21), transformants were used for heterologous expression of LigFA using LB-medium containing 100 μM FeCl2 and appropriate antibiotics. For induction of expression, 2 mM IPTG were added to overnight cultures, diluted ten-fold with fresh and pre-warmed LB-medium containing 100 μM FeCl2. For isolation of LigFA, an induction period of about two hours was found to be sufficient. Cells were harvested by centrifugation and resuspended in 10 mM sodium citrate buffer, pH 3.0, containing 100 μM FeCl2 and protease inhibitors as well as DNase. After sonication and separation from cell debris by centrifugation (10,000×g, 30 minutes, 4° C.) and overnight dialysis against the resuspension buffer, extracts were ultrafiltrated using a Centricon membrane (cut-off at 10 kDa, Amicon, Millipore). For purification, chromatography on a HiPrep 16/10 SP XL column (Amersham Pharmacia Biotech), equilibrated with 10 mM sodium citrate buffer, pH to 3.0, containing 100 μM $FeCl_2$ was used. Elution was done with a linear 0 to 1 M sodium chloride gradient. After peak fractions were gel filtrated after concentration by ultrafiltration (cut-off at 10 kDa) on a Superose gel filtration column pre-equilibrated with the above chromatography buffer containing 150 mM sodium chloride at a flow rate of 0.5 mL/min at 4° C.

EXAMPLE 3

DNA Ligation Using Acidophilic DNA Ligase (LigFA)

For DNA ligation, double-stranded DNA fragments, each comprising a complementary 3' overhang which were phosphorylated in 5' can be ligated in a total volume of 20 μL ligation buffer (100 mM Na-citrate, pH 3.0, 10 μM $Fe^{2+}$, 0.01-0.1 mM ATP, optionally 0.5 mM dithiothreitol), 0.1-5 micrograms DNA and 1 to 20 nmoles ligase. The reaction conditions are 40° C. for 5 minutes to 2 hours, the reaction can be stopped by the addition of stop buffer 98% (vol/vol) formamide, 10 mM EDTA, 0.05% bromophenol blue, 0.05% xylene cyanol, 0.2% SDS), followed by heating to 95° C. for 5 minutes or, alternatively, by adding stop/loading buffer (30% sucrose, 150 mM EDTA, 0.15% SDS, 0.03% bromophenol blue), and heating to 90° C. for 2 minutes.

When ligating two short oligonucleotides (35 bases and 25 bases) complementary to a 70 base oligonucleotide, using the same buffer at varying pH values, in a reaction volume of 20 μL, using 20 nM ligFA at 40° C. for 5 minutes, ligation was obtained. Oligonucleotides were phosphorylated in 5'.

Reactions were carried out in different buffers: HEPES, pH 7.0 (lane 1), HEPES, pH 6.0 (lane 2), sodium acetate, pH 5.0 (lane 3), sodium acetate, pH 4.0 (lane 4), sodium citrate, pH 3.0 to 0.5 (lanes 5 to 9, respectively). For detection of ligation, gel electrophoresis on a 10% denaturing polyacrylamide gel containing 7 M urea in TBE buffer (90 mM Tris-borate, 2.5 mM EDTA), staining with ethidium bromide. A densitometric reproduction of the gel region containing 60 base fragments is represented in FIG. 7.

When ligating 1 μg A DNA, digested with Sau3A, using 20 nM LigFA in a 20 μL reaction mixture, incubating for 2 hours at 40° C., heating for 2 minutes to 90° C., electrophoresis on a 0.8% agarose gel demonstrates ligation.

The densitometric analysis is given as FIG. 8: lane 1—λ DNA (no restriction, no ligation), lane 2—Sau3A restricted A DNA (no ligation), lanes 3 to 8—Sau3A restricted A DNA, re-ligated with LigFA at pH 2.0 to 7.0, lanes 9 to 14—Sau3A restricted A DNA, re-ligated with T4 ligase (buffer supplemented to 5 mM KCl and 15 mM $MgCl_2$) at pH 2.0 to 7.0.

EXAMPLE 4

Religation Activity of LigFA of Topoisomerase 2 Induced DNA Breaks

For a comparison of the religation activities of acidic LigFA to T4 ligase on DNA containing breaks caused by topoisomerase 2 (TOP 2), ligation activities were determined in vitro at various pH values. The results are shown in the non-denaturing agarose gel of FIG. 9.

DNA was incubated with TOP 2 to induce DNA damage. At pH 5.0, TOP 2 caused DNA breaks (lane 2) but not at pH 3.0 (lane 3). Using TOP 2 fragmented DNA (pH 5.0), religation activity of LigFA was clearly demonstrated using acidic reaction conditions (pH 4.0 to 2.0, lanes 7 to 10, respectively) by generation of larger DNA fragments. The comparative T4 ligase did not catalyse re-ligation of TOP 2 fragmented DNA at acidic pH values (lanes 13 to 17), but was active at pH above 7.5 (lane 18). However, at pH 7.5 TOP 2 did not show damaging activity (lane 19).

This example shows that acidic DNA ligases according to the invention can re-ligate TOP 2 induced DNA fragmentation at the pH value in which TOP 2 is active. Accordingly, these acidic DNA ligases, especially LigFA are able to enhance genomic stability at acidic pH values, at least against damaging activity of TOP 2.

EXAMPLE 5

Method for One-Tube Restriction and Ligation Reaction

The acidic ligase LigFA is especially suited for in vitro manipulations of DNA because a series of reaction steps which hitherto required the inactivation of enzymes and/or buffer changes between them can now be simplified to a one-tube reaction. As an example, restriction of DNA can be followed by subsequent ligation to the same or different DNA having hybridizing, i.e. sticky ends without separation of restriction enzymes when using an acidic DNA ligase of the invention. According to the invention, a restriction reaction can be stopped and restriction enzymes can be inactivated by changing the reaction's pH value to acidic, suitable for LigFA, for example to a pH of 2.0 to 3.0. When adding a sufficient amount of $Fe^{2+}$, DNA having compatible ends, wherein at least one species of DNA to be ligated is phosphorylated in 5', LigFA can be used to perform the ligation reaction.

For transformation, the ligation reaction may be precipitated by adding sodium acetate and isopropanol according to standard procedures in order to remove salts, and resolubilized in water, or taken directly for transformation of competent cells.

As an example, 1 μg DNA was digested with restriction enzymes in the appropriate restriction buffer in a total volume of 20 μL. Incubation was for 1 hour at 37° C. The restriction reaction was stopped by addition of the ten-times concentrated acidic ligation buffer (1 M sodium citrate, 100 μM $Fe^{2+}$, 0.1 mM ATP). As given below, some reactions were re-ligated by addition of LigFA to 20 nM for a total volume of 30 μL and incubation at 40° C. for 10 minutes.

The following reactions were performed and analyzed on 0.8% non-denaturing agarose gel, shown in FIG. 10: Lane 1—size marker (bp given on left side), lane 2—bacteriophage λ DNA (no restriction, no ligation) at pH 2.0, lane 3—bacteriophage λ DNA (no restriction, no ligation) at pH 7.0, lane 4—Sau3A digested bacteriophage λ DNA (no ligation) at pH 7.0, lane 5—Sau3A digested bacteriophage λ, DNA (no ligation) at pH 7.0, then acidified to pH 2.0, lanes 6-14—Sau3A digested bacteriophage λ DNA at pH 2.0, incubated with LigFA for 2, 5, 7.5, 10, 15, 30, 45, 60 and 90 min, respectively.

EXAMPLE 6

Cloning of Acidic Esterase from *Ferroplasma acidiphilum* (EstFA)

For cloning the gene encoding acidic esterase of *Ferroplasma acidiphilum* (EstFA), genomic DNA of *Ferroplasma acidiphilum* was subjected to PCR using an oligonucleotide containing an additional NsiI restriction site in combination with an oligonucleotide containing an additional XhoI site. Using the amplification conditions according to Example 1, an amplification product of approximately 930 base pairs could be isolated by agarose gel electrophoresis and extracted using the QiaEx II gel extraction kit.

After ligating into vector PCR 2.1 using the TOPO TA cloning kit, identified positive clones (kanamycin resistant, using X-Gal), inserts were sequenced using oligonucleotide primers M13 and rM13.

EXAMPLE 7

Heterologous Expression of Acidic Esterase (EstFA)

The genomic copy of the EstFA gene was gel-purified after restriction of a positive clone identified in example 5 using NsiI and XhoI and ligated into an expression vector (PET-3a, which had been predigested with the same endonucleases and dephosphorylated. After transformation into an *E. coli* expression host (DH5α), synthesis of EstFA could be induced when transformants were grown in liquid LB-medium containing 100 μM FeCl2 and appropriate antibiotics according to Example 2. For optimum expression of EstFA, esterase activity was checked using p-nitrophenol propionate as a substrate before cells were harvested by centrifugation. Harvested cells were resuspended in 10 mM sodium citrate buffer, pH 2.0, containing 100 μM FeCl2, protease inhibitors and DNase I grade H, incubated on ice, and sonicated. Cell debris was removed by centrifugation (10000×g, 30 minutes, 4° C.), dialyzed against the resuspension buffer and concentrated by ultrafiltration (cut-off of 10 kDa) to a total volume of 1 mL. Enzyme purification was done according to Example 2, using hydrolysis of the p-nitrophenol propionate as an indicator substrate for esterase.

EXAMPLE 8

Substrate Specificity of Acidic Esterase (EstFA)

Hydrolysis of p-nitrophenol propionate was observed spectrophotometrically at 405 nm, optionally in and 96-well plates. The substrate specificity of acidic esterase EstFA obtainable from *Ferroplasma acidiphilum* was characterized using the heterologously expressed EstFA of Example 6 (expressed in *E. coli*), using p-nitrophenol esters and triglycerides as summarised in following Table IV:

TABLE IV

Kinetic parameters of EstFA, expressed in *E. coli*, in hydrolysis of p-nitrophenol esters and triglycerides

| substrate | $K_{cat}$ ($s^{-1}$) | $K_m$ (mg · $ml^{-1}$) | $K_{cat}/K_m$ ($s^{-1}mg^{-1}$/ml) |
|---|---|---|---|
| p-nitrophenyl acetate | 860 ± 21 | 0.39 ± 0.08 | 2205.1 |
| p-nitrophenyl propionate | 1188 ± 25 | 0.20 ± 0.04 | 5940.0 |
| p-nitrophenyl butyrate | 2300 ± 30 | 1.75 ± 0.12 | 1314.3 |
| p-nitrophenyl caprylate | 239 ± 12 | 1.68 ± 0.12 | 142.3 |
| p-nitrophenyl caprate | 179 ± 4 | 4.30 ± 0.42 | 41.6 |
| p-nitrophenyl laurate | 120 ± 4 | 4.41 ± 0.38 | 27.2 |
| tributyrin | 1894 ± 27 | 1.75 ± 0.14 | 1082.3 |
| Triolein | 22 ± 1 | 6.10 ± 0.14 | 3.61 |

For an estimation of enantioselectivity of EstFA towards chiral esters and lactones, a number of primary and secondary alcohols as well as carboxylic acids and lactones were hydrolysed. Substrates and results are given in the following table.

TABLE V

Enantionselectivity of EstFA towards chiral esters and lactones

| substrate | % c | % e.e. | E | stereo-preference |
|---|---|---|---|---|
| primary or secondary alcohols | | | | |
| solketal butyrate | 29.0 | 74.46 | 9.2 | R |
| 1-phenyl ethylbutyrate | 36.2 | 33.7 | 2.4 | S |
| 2-methyl-glycidyl | 37.8 | 37.4 | 2.7 | S |
| menthyl acetate | 42.2 | 78.4 | 14.7 R | |
| chiral carboxylic acids (stereocenter α and β to carbonyl) | | | | |
| methyl-3-hydroxybutyrate | 26.2 | 98 | 42.8 R | |
| methyl-3-hydroxy-2-methylpropionate | 30.8 | 98 | 116.2 R | |
| alanine methylester | 8.71 | 2.5 | 3.8 | S |
| tryptophane methylester | 4.33 | 2.12 | 1.1 | R |
| methyl lactate | 3.4 | 2.38 | 1.1 | R |
| N-benzylester | 7.71 | 8.64 | 1.20 | R |
| lactones | | | | |
| pantolactone | 10.06 | 39.36 | 2.40 | S |
| dihydro-5-hydroxymethyl-2(3H)-furanone | 39.3 | 88.6 | 29.7 S | |

The above substrate specificities were tested in 96-well plates, using 100 mM citrate buffer (pH 2.0) in the presence of 5 μg pure EstFA. For the substrate, the concentrations between 10 nM and 10 mM were chosen. Progress of the reaction was followed by spectrophotometry using p-nitrophenol propionate as an indicator. The reaction was stopped after 10 hours by adjusting the pH to 8.0 by adding sodium hydroxide from a 100 mM stock solution and phenol red (0.8 mM) as a pH indicator. Activities and selectivities were examined according to Mam Fai Lui et al. (2001). Ester hydrolysis of enantiomerically pure esters was measured colorimetrically in 5.0 mM EPPS buffer (N-(2-hydroxyethyl) piperazine-N'-(3'-propanesulfonic acid) at pH 8.0 and phenol red after termination of the reaction.

EXAMPLE 9

Cloning of Glycosidases from *Ferroplasma acidiphilum* (αGluFA, GlyFA1 and GlyFA2)

From an expression library of *Ferroplasma acidiphilum* genomic DNA in *E. coli* (XL1-Blue MRF') using the bacteriophage λ based ZAP-Express kit (Stratagene), clones expressing a glycosidase were identified by their violet halo in NZY-agar containing 0.2% (wt/vol) sucrose and 1 mM $FeCl_2$ that had been poured as an overlay over the same agar and overlaid with iodine solution (Sigma). Phagemids isolated from positive clones were maintained and expressed in *E. coli* (strain XLOLR), grown in LB-medium containing 100 µM $FeCl_2$ and 50 µg/mL kanamycin.

As a result, three different genes could be identified, namely αGluFA, GlyFA1 and GlyFA2. For expression of acidic glycosidases, induction was done on transformed *E. coli* according to Example 1, followed by an enzyme purification process according to Example 2.

EXAMPLE 10

Enzymatic Activity of a Glucosidase Obtainable from *Ferroplasma acidiphilum* (αGluFA)

Hydrolytic activity was generally measured using maltose as a substrate and measuring reducing sugars released from a 1% (wt/vol) substrate solution by HPLC. For hydrolysis assays, 100 mM sodium citrate buffer, pH 3.5, 100 µM FeCl2 was used at 40° C., optionally using sucrose as a substrate. Reactions were stopped by heating to 80° C. for 15 minutes, samples were diluted 1:5 (vol/vol) with water, centrifuged and filtered (0.45 µm) prior to analysis by HPLC on a 4.6×250 mm Lichrosphere-NH2 column (Merck). The mobile phase was acetonitrile:$H_2O$, 75:25 (vol/vol) at a flow rate of 0.7 mL/min at a temperature of 25° C. For detection, a refraction index detector (Varian) was used integration was carried out using the Millennium software. All enzyme reactions were set to be linear in respect to time and protein concentration. For correction of spontaneous hydrolysis of substrate, sample blanks were used and substracted for enzymatic reaction measurements. For the determination of sucrose hydrolysis, a continuous spectrophotometric assay could be used measuring reducing sugars reacted with dinitrosalicylic acid (Sumner and Howell, 1935).

EXAMPLE 11

Hydrolysis of Various Substrates by αGluFA

A variety of glycosidic substrates were examined for hydrolysis by αGluFA and kinetic constants were determined. For the assay, heterologously expressed αGluFA was incubated in 100 mM sodium citrate buffer, pH 3.0, containing 1% substrate, 100 µM FeCl2 and 5 µg αGluFA. The reaction was allowed to proceed for 30 minutes at 50° C., then stopped by heating to 80° C. for 15 minutes. Analysis was done by HPLC. Sample blanks were used for correction of spontaneous release of reducing sugar.

As substrates, sucrose, starch, amylose, amylopectin, pullulan and dextrin were used, the release of reducing sugars could also be determined by the dinitrosalicylic acid method, i.e. adding dinitrosalicylic acid solution to the reaction mixture, heating to 85° C. for 30 minutes, dilution with water and measuring absorbance at 450 nm. Activity towards p-nitrophenol α/β diglucopyranoside could be measured spectrophotometrically by following the absorbance at 346 nm using a molar extinction coefficient of 4800.

Using HPLC, kejibiose, nigeriose, isomaltose, isomaltotriose, trehalose and malto oligosaccharides from G4 to G7 were hydrolysed. Results for some substrates are given in the following Table VI.

TABLE VI

| Kinetic parameters of αGluFA in hydrolysis. | | | |
| --- | --- | --- | --- |
| Substrate | $K_{cat}$ $(s^{-1})$ | $K_m$ $(mg \cdot ml^{-1})$ | $K_{cat}/K_m$ $(s^{-1}mg^{-1}/ml)$ |
| soluble starch | 94.0 ± 11 | 0.11 ± 0.02 | 854.5 |
| amylose | 126.0 ± 7.5 | 7.49 ± 0.88 | 16.8 |
| amylopectin | 89 ± 10.5 | 1.05 ± 0.19 | 84.8 |
| maltooligossacharides | 13.0 ± 1.1 | 0.350 ± 0.04 | 37.1 |
| dextrin | 93.0 ± 11 | 0.221 ± 0.03 | 420.8 |
| maltose | 4.2 ± 0.2 | 0.100 ± 0.02 | 42.0 |
| pullulan | 2.8 ± 0.1 | 11.0 ± 0.1 | 0.3 |

These data show that αGluFA selectively synthesizes maltotriose, i.e. predominantly forms α1,4-linkages at a pH of 3.0 for concentrations of up to 300 g/L maltotriose. However, maltotetrose was synthesized only in small amounts.

EXAMPLE 12

Synthesis of Oligosaccharides Using αGluFA

αGluFA is also suitable for the transfer of glucosyl groups from maltose to selectively produce a maltotriose. For transglucosylation of maltose by αGluFA, 600 g/L maltose in 0.2 M sodium citrate buffer, pH 3.0, were reacted with 5 µg/mL purified αGluFA at 50° C. The reaction was followed by HPLC measurements. The percentage of transglucosylated maltose, resulting in maltotriose is given in the following Table VII.

TABLE VII

| Transglucosylation of maltose catalyzed by αGluFA | | | | |
| --- | --- | --- | --- | --- |
| reaction time (rain) | glucose (g/L) | maltose (g/L) | maltotriose (g/L) | percentage of maltose transglycosylated |
| 0 | 0 | 600 | 0 | — |
| 5 | 59 | 456 | 88 | 70.3 |
| 10 | 76 | 402 | 122 | 72.7 |
| 20 | 112 | 302 | 186 | 74.5 |
| 30 | 153 | 199 | 248 | 73.3 |
| 60 | 165 | 159 | 276 | 74.7 |
| 180 | 185 | 111 | 304 | 74.0 |

As can be taken from Table VII, the percentage of transglucosylated maltose is very high (more than 70%) and it is interesting to see that progress of the reaction does not affect the transglucosylation ratio, i.e. a decrease of the maltose concentration does not result in hydrolysis of maltotriose.

This example shows that αGluFA has a high a transglucosylation capability even at low or moderate maltose concentrations.

The kinetic parameters of the transglucosylation reaction catalyzed by αGluFA was measured in the assay described above.

TABLE VIII

Kinetic parameters $k_{cat}/K_m [s^{-1} \cdot mM^{-1}]$ of αGluFa, GlyFA1 and GlyFA2 glycosidases from *F. acidiphilum*

| substrate | αGluFA | GlyFA1 | GlyFA2 |
|---|---|---|---|
| sucrose (α-D-Glc-(1 −> 2)-α-D-Fru) | 293.0 ± 44.0 | 142.0 ± 27.0 | 142.0 ± 30.0 |
| maltose (α-D-Glc-(1 −> 4)-D-Glc) | 197.0 ± 20.0 | 73.0 ± 12.0 | 101.0 ± 21.0 |
| maltotriose (α-D-Glc-(1 −> 4)-α-D-Glc-(1 −> 4)-D-Glc) | 18.8 ± 1.8 | 28.0 ± 3.1 | 37.0 ± 4.3 |
| maltotetrose (α-D-Glc-(1 −> 4)-α-D-Glc-(1 −> 4)-α-D-Glc-(1 −> 4)-D-Glc) | 0.3 ± 0.1 | 0.6 ± 0.1 | 0.1 ± 0.01 |
| p-nitrophenyl α-D-glucopyranoside | 293.0 + 44.0 | 142.0 ± 27.0 | 142.0 ± 30.0 |

Data are means ± SDs

From Table VIII it is evident that the preference for substrate hydrolysis is sucrose>maltose>maltotriose>maltotetrose for the acidic glycosidases tested.

The invention claimed is:

1. An isolated DNA ligase, comprising the amino acid sequence of SEQ ID NO: 2.

2. The isolated DNA ligase of claim 1, wherein the amino acid sequence of SEQ ID NO: 2 is encoded by the DNA sequence of SEQ ID NO: 1.

3. A process for an enzymatic conversion using an enzyme, wherein the enzyme is the isolated DNA ligase of claim 1 and wherein the enzymatic conversion is a ligation of nucleic acids.

4. The process of claim 3, further comprising acidifying the pH of a DNA preparation to a pH of 5 or lower, wherein DNA modifying enzymes active at pH values above 5 are stopped; and further comprising addition of the isolated DNA ligase.

* * * * *

UNITED STATES PATENT AND TRADEMARK OFFICE
CERTIFICATE OF CORRECTION

| | |
|---|---|
| PATENT NO. | : 8,003,357 B2 |
| APPLICATION NO. | : 11/885109 |
| DATED | : August 23, 2011 |
| INVENTOR(S) | : Golyshina et al. |

It is certified that error appears in the above-identified patent and that said Letters Patent is hereby corrected as shown below:

In the Specification:

| | |
|---|---|
| Col. 2, line 63 | Delete "genomiccoding" and insert --genomic coding-- therefor. |
| Col. 8, line 12 | Delete "1 μg A DNA" and insert --1 μg λ DNA-- therefor. |
| Col. 8, line 17 | After "restricted" delete "A" and insert --λ-- therefor. |
| Col. 8, line 18 | After "restricted" delete "A" and insert --λ-- therefor. |
| Col. 8, line 20 | After "restricted" delete "A" and insert --λ-- therefor. |
| Col. 9, line 23 | Delete "λ, DNA" and insert --λ DNA-- therefor. |
| Col. 9, line 64 | Delete "I grade H" and insert --I grade II-- therefor. |
| Col. 11, line 47 | Delete "was used integration" and insert --was used; integration-- therefor. |
| Col. 12, line 54 | In Table VII, delete "reaction time (rain)" and insert --reaction time (min)-- therefor. |

Signed and Sealed this
Twentieth Day of December, 2011

David J. Kappos
*Director of the United States Patent and Trademark Office*